US008268590B2

(12) United States Patent
Kim et al.

(10) Patent No.: US 8,268,590 B2
(45) Date of Patent: Sep. 18, 2012

(54) NON-ACTIVATED POLYPEPTIDES HAVING A FUNCTION OF TISSUE REGENERATION AND METHOD FOR PREPARING THE SAME

(75) Inventors: Jung Moon Kim, Seoul (KR); Jung Kook Kim, Seoul (KR); Tae Han Kim, Seongnam-si (KR); Jong Suk Lee, Seoul (KR); Jong In Yook, Seoul (KR)

(73) Assignees: Jung Moon Kim, Seoul (KR); Jung Kook Kim, Seoul (KR); Tae Han Kim, Gyeonggi-do (KR); Jong Suk Lee, Seoul (KR)

( * ) Notice: Subject to any disclaimer, the term of this patent is extended or adjusted under 35 U.S.C. 154(b) by 0 days.

(21) Appl. No.: 11/781,243

(22) Filed: Jul. 21, 2007

(65) Prior Publication Data
US 2008/0064065 A1 Mar. 13, 2008

Related U.S. Application Data

(62) Division of application No. 10/560,329, filed as application No. PCT/KR2005/003660 on Nov. 2, 2005, now abandoned.

(30) Foreign Application Priority Data

Mar. 30, 2005 (KR) .................. 10-2005-0026246

(51) Int. Cl.
C12P 21/06 (2006.01)
C12Q 1/58 (2006.01)
C12N 1/10 (2006.01)
(52) U.S. Cl. .................. 435/69.7; 435/12; 536/23.4
(58) Field of Classification Search .................. None
See application file for complete search history.

(56) References Cited

U.S. PATENT DOCUMENTS

| | | | |
|---|---|---|---|
| 4,294,753 A | 10/1981 | Urist | |
| 4,968,590 A | 11/1990 | Kuberasampath et al. | |
| 5,013,649 A | 5/1991 | Wang et al. | |
| 5,106,626 A | 4/1992 | Parsons et al. | |
| 5,106,748 A | 4/1992 | Wozney et al. | |
| 5,166,058 A | 11/1992 | Wang et al. | |
| 5,187,076 A | 2/1993 | Wozeny et al. | |
| 5,187,623 A | 2/1993 | Ibaraki | |
| 5,208,219 A | 5/1993 | Ogawa et al. | |
| 5,258,494 A | 11/1993 | Oppermann et al. | |
| 5,266,683 A | 11/1993 | Oppermann et al. | |
| 5,284,756 A | 2/1994 | Grinna et al. | |
| 5,399,346 A | 3/1995 | Anderson et al. | |
| 6,531,450 B2 | 3/2003 | Hotten et al. | |
| 6,593,109 B1 | 7/2003 | Israel et al. | |
| 6,673,574 B2 | 1/2004 | Stern et al. | |
| 6,764,994 B1 | 7/2004 | Hotten et al. | |
| 2003/0181378 A1 | 9/2003 | Makishima et al. | |
| 2004/0197867 A1 | 10/2004 | Titus et al. | |
| 2005/0147971 A1 | 7/2005 | Lee et al. | |
| 2007/0105762 A1 | 5/2007 | Kim et al. | |

FOREIGN PATENT DOCUMENTS

| | | |
|---|---|---|
| CN | 1546668 A | 11/2004 |
| WO | 9633215 A1 | 10/1996 |
| WO | 02096952 A2 | 12/2002 |
| WO | 03012111 A2 | 2/2003 |
| WO | 2005111058 A1 | 11/2005 |

OTHER PUBLICATIONS

Nagahara et al., Nature Medicine, 4(12):1448-1452 Dec. 1998.*
Wozney et al., Science, 242(4885):1528-1534, published Dec. 1988.*
Sugita et al., "Comparative study on transduction and toxicity of protein transduction domains", British Journal of Pharmacology, 153:1143-1152, Jan. 28, 2008.*
Bernstein, Emily, et al., "Role for a bidentate ribonuclease in the initiation step of RNA interference", "Nature", Jan. 18, 2001, pp. 363-366, vol. 409.
Derynck, Rik, et al., "Smad-dependent and smad-independent pathways in TGF-beta family signalling", "Nature", Oct. 9, 2003, pp. 577-584, vol. 425.
Nagahara, Hikaru, et al., "Transduction of full-length TAT fusion proteins into mammalian cells: TAT-p27kip1 induces cell migration", "Nature Medicine", Dec. 1998, pp. 1449-1452, vol. 4, No. 12.
Ruppert, Rainer, et al., "Human bone morphogenetic protein 2 contains a heparin-binding site which modifies its biological activity", "Eur. J. Biochem.", 1996, pp. 395-302, vol. 237.
Scheufler, Clemens, et al., "Crystal structure of human bone morphogenetic protein-2 at 2.7 a resolution", "J. Mol. Bio.", 1999, pp. 103-115, vol. 287.
Schwarze, Steven R., et al., "In Vivo Protein Transduction: Delivery of a Biologically Active Protein into the Mouse ", "Science", Sep. 3, 1999, pp. 1569-1572, vol. 285, No. 5433.
Schwarze, Steven R., et al., "Protein transduction: unrestricted delivery into all cells?", "Trends in Cell Biology", Jul. 2000, pp. 290-295, vol. 10.

(Continued)

Primary Examiner — Daniel E Kolker
Assistant Examiner — Stacey MacFarlane
(74) Attorney, Agent, or Firm — Hultquist PLLC; Kelly K. Reynolds; Steven J. Hultquist

(57) ABSTRACT

Non-activated tissue-regeneration polypeptides (TRPs) and their preparation methods are disclosed. The TRPs include: a protein transduction domain (PTD) making the polypeptides to permeate a cell membrane without cell membrane receptors; a furin activation domain (FAD) which has at least one proprotein convertase cleavage site and which can be cleaved by the proprotein convertase and activate a tissue regeneration domain (TRD) in cells; and a tissue regeneration domain (TRD) which can be activated by the proprotein convertase cleavage of the FAD to stimulate the growth or formation of tissues or to induce the regeneration of tissues. The TRPs can be mass-produced by cultured bacteria, such as recombinant *E. coli*, are in a non-activated state before in vivo administration, and their separation, purification, handling, storage and administration are simple and convenient. The in vivo administration of the TRPs is useful to stimulate the formation or regeneration of tissues, such as bones or cartilages, or to improve the fibrosis and cirrhosis of organs, such as kidneys, liver, lungs and heart by pharmacological mechanisms completely different from those of prior rhBMPs or TGF-β proteins.

5 Claims, 16 Drawing Sheets

OTHER PUBLICATIONS

Storm, Elaine E., et al., "Limb alterations in brachypodism mice due to mutations in a new member of the TGFbeta-superfamily", "Nature", Apr. 14, 1994, pp. 639-643, vol. 368.

Thomas, Gary, "Furin at the cutting edge: from protein traffic to embryogenesis and disease", "Nature Reviews Molecular Cell Biology", Oct. 2002, pp. 753-766, vol. 3.

Vinall, Ruth L., et al., "The effect of BMP on the expression of cytoskeletal proteins and its potential relevance", "The Journal of Bone and Joint Surgery", 2001, pp. (S1) 63-69, vol. 83A, No. 1.

Wadia, Jehangir S., et al., "Modulation of cellular function by TAT mediated transduction of full length proteins", "Current Protein and Peptide Science", 2003, pp. 97-104, vol. 4.

Yamashita, Hidetoshi, et al., "Growth/differentiation factor-5 induces angiogenesis in vivo", "Experimental Cell Research", 1997, pp. 218-226, vol. 235.

Zeisberg, Michael, et al., "BMP-7 counteracts TGF-beta1-induced epithelial-to-mesenchymal transition and reverses chronic renal injury", "Nature Medicine", Jul. 2003, pp. 964-968, vol. 9, No. 7.

Bernstein, Emily, et al., "Role for a bidentate ribonuclease in the initiation step of RNA interference", "Nature", Jan. 2001, pp. 363-366, vol. 409, No. 6818.

Constam, D.B., et al, "Regulation of bone morphogenetic protein activity by pro domains and proprotein convertases", "J. Cell Biol.", Jan. 1999, pp. 139-149, vol. 144, No. 1.

Bettaccini, A. et al., "Proliferative activity of extracellular HIV-1 Tat protein in human epithelial cells: expression profile of pathogenetically relevant genes," Apr. 2005, BMC Microbiology 2005, vol. 5, No. 20.

Granjeiro, J. et al. , "Bone morphogenetic proteins: from structure to clinical use", "Braz J Med Biol Res", 2005, p. 2005 vol. 38, No. 10.

Xiao, Y. et al. , "Bone morphogenetic protein", "Biochemical and Biophysical Research Communications ", 2007, pp. 550-553, vol. 362.

Miyazono,K. et al., "Latent High Molecular Weight Complex of Transforming Growth Factor Beta 1", "The Journal of Biological Chemistry", 1988, pp. 6407-6415, vol. 263, No. 13.

Urist M., "Bone: formation by autoinduction.", "Science. (Abstract Only)", Nov. 12, 1965, pp. 893-899, vol. 150, No. 698.

Wozney, J., "Bone morphogenetic proteins", "Prog Growth Factor Res. (Abstract Only)", 1989, pp. 267-280, vol. 1, No. 4.

Cui, Yanzhen, et al., "The activity and signaling range of mature BMP-4 is regulated by sequential cleavage at two sites within the prodomain..", "Genes Dev.", Nov. 1, 2001, pp. 2797-2802, vol. 15, No. 21.

Degnin, Catherine, et al., "Cleavage within the prodomain direct intracellular trafficking and degradation of mature bone morphogenetic protein-4", "Mol. Biol. Cell", Nov. 2004, pp. 5012-5020, vol. 15, No. 11.

Derynck, Rik and Zhang, Ying E., "Smad-dependent and smad-independent pathways in TGF-beta family signalling", "Nature", Oct. 2003, pp. 577-584, vol. 425, No. 6958.

Ganju, A., "Isthmic spondylolisthesis", "Neurosurg. Focus", Jul. 2002, pp. E1, vol. 13, No. 1.

Griffith, D.L., et al., "Three-dimensional structure of recombinant human osteogenic protein 1: structural paradigm for the transforming growth..", "Proc. Natl. Acad. USA", Jan. 23, 1996, pp. 878-883, vol. 93, No. 2.

Jean, Francois, et al., "Alpha1-Antitrypsin Portland, a bioengineered serpin highly slective for furin: application as an antipathogenic agent", "Proc. Natl. Acad. Sci. USA", Jun. 23, 1998, pp. 7293-7298, vol. 95, No. 13.

Kalluri, Raghu, et al., "Epithelial-mesenchymal transition and its implications for fibrosis", "J. Clin. Invest.", Dec. 2003, pp. 1176-1784, vol. 112, No. 12.

Leighton, Mat, et al., "Paird basic/furin-like proprotein convertase cleavage of pro-BMP-1 in the trans-golgi network", "Journal of Biological Chemistry", May 16, 2003, pp. 18478-18484, vol. 278, No. 20.

Nagahara, Hikaru, et al., "Transduction of full-length TAT fusion proteins into mammalian cells: TAT-p27Kip1 induces cell migration", "Nat. Med.", Dec. 1998, pp. 1449-1452, vol. 4, No. 12.

Reddi, A.H., "Bone morphogenetic protiens: from basic science to clinical applications", "J Bone Joint Surg Am.", 2001, pp. S1-S6, vol. 83-A Suppl 1, No. Pt 1.

Ruppert et al., "Human bone morphogenetic protein 2 contains a heparin-binding site which modifies its biological activity", "Eur. J. Biochem.", Apr. 1996, pp. 295-302, vol. 237, No. 1.

Scheufler, C., et al., "Crystal structure of human bone morphogenetic protein-2 at 2.7 A resolution", "J. Mol. Biol.", Mar. 19, 1999, pp. 103-115, vol. 287, No. 1.

Schwarz, Dianne S., et al., "Asymmetry in the assembly of the RNAi enzyme complex", "Cell", Oct. 17, 2003, pp. 199-208, vol. 115, No. 2.

Schwarze, Steven R., et al., "In vivo protein transduction: delivery of a biologically active protein into the mouse", "Science", Sep. 3, 1999, pp. 1569-1572, vol. 285, No. 5433.

Schwarze, S.R., et al., "Protein transduction: unrestricted delivery into all cells?", "Trends Cell Biol.", Jul. 1, 2000, pp. 290-295, vol. 10, No. 7.

Storm, Elaine E., et al., "Limb alterations in Brachypodism mice due to mutation in a new member of the TGFbeta-superfamily", "Nature", Apr. 14, 1994, pp. 639-643, vol. 368, No. 6472.

Thomas, Gary, "Furin at the cutting edge: from protein traffic to embryongenesis and disease", "Nat. Rev. Mol. Cell Biol.", Oct. 2002, pp. 753-766, vol. 3, No. 10.

Wadia, J.S., et al., "Modulation of cellular function by TAT mediated transduction of full length proteins", "Curr. Protein Pept. Sci.", Apr. 2003, pp. 97-104, vol. 4, No. 2.

Wang, E.A., et al., "Recombinant human bone morphogenetic protein induces bone formation", "Proc. Natl. Acad. Sci. USA", Mar. 15, 1990, pp. 2220-2224, vol. 87, No. 6.

Yamashita, Hidetoshi, et al., "Growth/Differentiation Factor-5 induces angiogenesis in vivo", "Exp. Cell Res.", Aug. 25, 1997, pp. 218-226, vol. 235, No. 1.

Zeisberg, Michael, et al., "BMP-7 counteracts TGF-beta 1-induced epithelial-to-mesenchymal transition and reverses chronic renal injury", "Nat. Med.", Jul. 2003, pp. 964-968, vol. 9, No. 7.

Zeisberg, Michael, et al., "Bone morphongenic protein-7 induces mesenchymal to epithelial transition in adult renal fibroblasts and facilitates . . .", "J. Biol. Chem.", Mar. 4, 2005, pp. 8094-8100, vol. 280, No. 9.

* cited by examiner

NON-ACTIVATED POLYPEPTIDES HAVING A FUNCTION OF TISSUE REGENERATION AND METHOD FOR PREPARING THE SAME

CROSS-REFERENCE TO RELATED APPLICATIONS

This is a divisional application, filed under the provisions of 35 USC 120, of U.S. patent application Ser. No. 10/560,329 now abandoned. U.S. patent application Ser. No. 10/560,329 was filed on Dec. 10, 2005 under the provisions of 35 USC 371 and published on May 10, 2007 as U.S. patent application Ser No. 2007/0105762 and claims the priority of International Patent Application No. PCT/KR05/003660 filed Nov. 2, 2005 and published on May 10, 2006 as WO/2006/104306. International Patent Application No. PCT/KR05/003660 in turn claims priority of Korean Patent Application No. 10-2005-0026246 filed Mar. 30, 2005. The disclosures of all of such applications are hereby incorporated herein by reference in their respective entireties.

TECHNICAL FIELD

The present invention is related to non-activated tissue-regenerative polypeptides (TRPs) and the methods for preparing the TRPs, the tissue regenerative polypeptides, which contain: a protein transduction domain (PTD) making the polypeptides to permeate a cell membrane without cell membrane receptors; a furin activation domain (FAD) which has at least one proprotein convertase cleavage site and which can be cleaved by the proprotein convertase and can activate a non-activated tissue regeneration domain (TRD) in cells; and a non-activated tissue regeneration domain (TRD) which can be activated through the cleavage of the FAD by the proprotein convertase in cells and which can stimulate the growth or formation of tissues or to induce tissue regeneration.

BACKGROUND ART

It is known that bone morphogenetic proteins (BMPs) stimulate the healing of bone defects in mammals or primates, and particularly are secreted in bone cells to induce bone formation through receptors present in the adjacent cell membranes, when used with collagen or biodegradable polymers in demineralization conditions. The hBMPs are a group of proteins having similarity to each other, and are known to have more than 14 members, including hBMP2 through hBMP15 until now. The hBMP2, 3, 4, 6, 7 and 14 are known to have the medical efficacy of inducing bone regeneration.

Among them, the hBMP2 has been known to be the most effective bone morphogenetic protein. There have been a lot of studies on the medical effects and applications of BMP proteins. The BMP7 is known to not only suppress the fibrosis of organs by antagonistic action of TGF-β1, but also induce the regeneration of organs (*Nature Med.*, 9:964, 2003; *J. Biol. Chem.*, 280:8094, 2005). It is known that the BMP14, (GDF-5, growth/differentiation factor-5: MP-52) shows the function of effectively healing skin wounds and aiding the healing of gastric or duodenal ulcer when administered to human beings or mammals (U.S. Pat. No. 6,764,994; *Nature*, 368:639, 1994; *Exp. Cell Res.*, 235:218, 1997; *Neurosurg Focus*, 13:1, 2002; U.S. Pat. No. 6,531,450). In the case of liver or kidney cirrhosis, the BMPs are also known to antagonize TGF-β to inhibit the formation of fibrous tissue and induce the recovery of normal tissue. Namely, the BMPs may function not only to stimulate the formation of bones or cartilages but also to regenerate the skin or regenerate gastrointestinal tissue, unlike the terminological definition of BMP.

As an old method for preparing BMPs, a method of extracting BMPs from demineralized animal bone tissue using natural salt (U.S. Pat. No. 4,294,753) has been attempted, but the method has problems in that the preparation efficiency is too low for mass production. A method was developed in early 1990s for separating and purifying the active recombinant hBMP2 after culturing CHO cells transformed with a BMP gene (*Proc. Natl. Acad. Sci.*, 87:2220, 1990). Since then, the mass production of BMPs has been possible (U.S. Pat. Nos. 4,968,590; 5,106,626; 5,106,748; 5,166,058; 5,187,076; 5,187,623; 5,208,219; 5,258,494; 5,266,683; 5,284,756; 5,399,346; and 6,593,109).

However, the methods for preparing recombinant hBMP2 and hBMP7 using the transformed CHO cells have problems in that the culturing of a large amount of CHO cells is required to obtain enough amount of active rhBMP2 or rhBMP7. The separation and purification steps are very complicated, and the production cost is very high. Also, these methods have a common problem that the biological activity of the proteins is reduced during the separation, purification, storage, medication and/or administration processes. To improve a part of the shortcomings of these methods of preparing recombinant BMPs by culturing animal cells, Biopharm company recently developed a method for preparing rhBMP14(MP-52) by culturing recombinant *E. coli* at lower cost (US 2003/0181378; WO 96/33215). In this method of preparing the rhBMP14, however, the step of separating and purifying rhBMP14 in the form of an activated protein is still complicated and inconvenient. The problem of activity reduction of the prepared *E. coli* recombinant protein has still not been solved for the separation, purification, storage, handling, and/or administration steps.

Moreover, in producing active BMPs in recombinant *E. coli* as in the case of the prior Biopharm's method, there is a limitation on the selection and designing of the biochemical structures of BMPs. Even if it is possible to prepare a protein having the structure like rhBMP14, using the Biopharm's method, it shall not be possible to practically prepare the BMPs having similar biochemical structures like active rhBMP2, rhBMP4, rhBMP7, etc.

In the case of rhBMP-2, which is commercially available and is medically used for, e.g., spine fusion, it is being sold for as high as several thousand US dollars per mg in the year 2005. Despite that the rhBMPs have various latent potencies for numerous patients who need spine fusion operations, or who need regenerating gastric ulcer or liver cirrhosis, the clinical application of BMPs has been limited because of the extremely high cost and the inconveniences and activity loss in the storage, handling and administration.

Accordingly, in the art, there has been an urgent and strong need for the development of new kinds of biochemical drug substances which would provide equal or higher biomedical efficacy than those of rhBMPs or TGF-βs, and which can be produced at significantly lower costs than those for previously known proteins, and which can fundamentally solve the inconveniences and the activity reduction problem in the separation, purification, storage, handling, and administration steps.

Accordingly, the present inventors have spent extensive time and efforts to develop a group of new polypeptides, which can fundamentally solve the problems in the previously known activated proteins produced for stimulating the formation of bones or cartilages, or the regeneration of biological tissues including the skin wounds, ulcer, and/or liver cirrhosis. The new polypeptides have new biochemical structures and provide biomedical efficacy by new pharmacological mechanisms. The new kind of polypeptides can be directly medicated to human patients to stimulate the formation or regeneration of bones or cartilages or to improve or regenerate the fibrosis or cirrhosis of organs, such as kidneys, liver, lungs and heart, by new pharmacological mechanisms. The newly developed polypeptides are kept in a non-activated state in steps of the separation, purification, storage, and handling before administration. The new polypeptides are designed so that they shall be activated in vivo after administration to patients.

Namely, the present inventors have developed a new group of non-activated tissue-regeneration polypeptides (TRPs) containing: a protein transduction domain (PTD) making the proteins to permeate cell membranes; a furin activation domain (FAD) which has at least one proprotein convertase cleavage site and which can be cleaved by the proprotein convertase and can activate a non-activated tissue regeneration domain (TRD) in cells; and a non-activated TRD which can be activated by the proprotein convertase cleavage of the FAD. The in vivo activated polypeptides are designed to stimulate the growth or formation of tissue or to induce the regeneration of tissue. Also, the present inventors have found that the production cost of the present TRPs are significantly lower than those of the existing active proteins such as rhBMPs. It is much easier to store, handle, and administer the present TRPs than the existing rhBMPs. The present TRPs provide biomedical efficacies by new pharmacological mechanisms. Specifically the TRPs permeate cell membranes without help from receptors. They are cleaved by furin in cells and then activated. The activated proteins are secreted out of the cells in large amount, and then they stimulate cell membrane receptors for bone formation or tissue regeneration. On the basis of these new findings, the present invention has been completed.

SUMMARY OF THE INVENTION

A primary object of the present invention is to provide non-activated TRPs having biochemical structures, characteristics and pharmacological mechanisms that are completely different from the previously known active rhBMP proteins. The new non-activated TRPs are designed so that they can be administered directly into the human body to stimulate the formation or regeneration of bones and cartilages or to improve the fibrosis and cirrhosis of organs, such as kidneys, liver, lungs and heart, and ultimately to induce tissue regeneration. The present invention also provides practical production and preparation methods for the TRPs.

Another object of the present invention is to provide a new drug composition for stimulating the formation or regeneration of tissues, such as bones and cartilages, or a new drug composition for improving the fibrosis or cirrhosis of organs, such as kidneys, liver, lungs and heart, the composition containing said non-activated TRPs.

To achieve the above objects, in one aspect, the present invention provides a non-activated tissue-regeneration polypeptides (TRPs) containing: (a) a protein transduction domain (PTD) making the polypeptides to permeate cell membranes without cell membrane receptors; (b) a furin activation domain (FAD) which has at least one proprotein convertase cleavage site and which can be cleaved by the proprotein convertase and can activate a non-activated tissue regeneration domain (TRD) in cells; and (c) a non-activated TRD which can be activated in vivo by the proprotein convertase cleavage of the FAD. The in vivo activated proteins are designed to stimulate the growth or formation of tissues or to induce the regeneration of tissues.

In another aspect, the present invention provides a recombinant vector inserted with an FAD-encoding base sequence in front of the 5' region of TRD-encoding DNA, a PTD base sequence, a base sequence for tagging, and at least four histidine-encoding base sequences for separation and purification. The present invention also provides bacteria transformed with the said recombinant vectors.

In still another aspect, the present invention provides a method for preparing non-activated TRPs, comprising the steps of: (a) culturing the said transformed bacteria to express a [PTD-FAD-TRD] polypeptide; and (b) centrifuging the culture broth, and then removing the two-dimensional or three-dimensional structure of the polypeptides or converting the two-dimensional or three-dimensional structure to one-dimensional linear structure by addition of a urea solution into the supernatant and cell pellet, and then purifying the [PTD-FAD-TRD] polypeptide.

In the present invention, the proprotein convertase may preferably be furin but is not limited thereto. Examples thereof include PC7, PC5/6A, PC5/6B, PACE4, PC1/3, PC2 and PC4.

Also, the TRD may preferably be represented by an amino acid sequence selected from the group consisting of SEQ ID NOs: 1 to 13, but is not specifically limited if it is a secreted protein showing the activity to stimulate the growth or formation of tissue or to induce tissue regeneration following the furin cleavage. Examples thereof include polypeptides such as BMPs, TGF-β, β-NGF (β-nerve growth factor), β-amyloid, ADAMs (a disintergrin and metalloproteinase-like), TNF-α, MMPs (matrix metalloproteinases), and insulin-like growth factor (IGF-1).

The FAD may preferably be represented by an amino acid sequence selected from the group consisting of SEQ ID NOs: 14 to 26, but is not specifically limited if it has a proprotein convertase cleavage site and if it can be cleaved by the proprotein convertase in cells to activate the TRD. Also, the PTD may preferably be selected from the group consisting of TAT, drosophila melanogaster-derived Antp peptide, VP22 peptide and mph-1-btm, but is not limited thereto.

In the inventive method for preparing the non-activated TRPs, the purification step may preferably comprise the substeps of binding the polypeptides to nickel-titanium beads, washing the beads with the same solution, and then eluting the beads with imidazole and a high-salt buffer solution, but is not limited thereto.

The non-activated TRPs according to the present invention have no three-dimensional stereoregularity that are possessed in common by the previously known active BMPs. The TRPs are not biologically active by themselves yet before administered into patients. When the non-activated TRPs are administered to the human beings or mammals, however, the proprotein convertase cleavage sites of FAD in the TRPs are cleaved by proprotein convertase present in living cells, whereby TRD is activated, and the activated TRD is secreted out of the cells, thereby showing the desired tissue regeneration potencies. The TRPs according to the present invention are preferably in the form of a fusion polypeptide of PTD, FAD and TRD. The inventive TRPs have a function to stimulate the formation or regeneration of tissues, such as human bones and cartilages, or to improve the fibrosis or cirrhosis of organs, such as kidneys, liver, lungs and heart, and ultimately to induce the regeneration of original tissue.

Accordingly, the present invention provides a new drug composition which contains the non-activated TRP as an active ingredient and which stimulates the formation or regeneration of tissue by new pharmacological mechanisms completely different from those of previously known protein medicines having uses similar thereto. In the present invention, the tissues may preferably be bone or cartilage. Furthermore, the present invention provides a new drug composition for improving the fibrosis or cirrhosis of organs, which contains the non-activated TRP as an active ingredient. The inventive composition may suitably contain, in addition to TRP, other growth factors, such as TGF-β (transforming growth factor-β), IGF (insulin-like growth factor), PDGF (platelet-derived growth factor), and FGF (fibroblast growth factor), in which case the therapeutic effect of the composition can be significantly increased.

Other features and embodiments of the present invention will be more clearly understood from the following detailed description and accompanying claims.

DETAILED DESCRIPTION OF THE INVENTION, AND PREFERRED EMBODIMENTS THEREOF

Figures 1A, 1B:
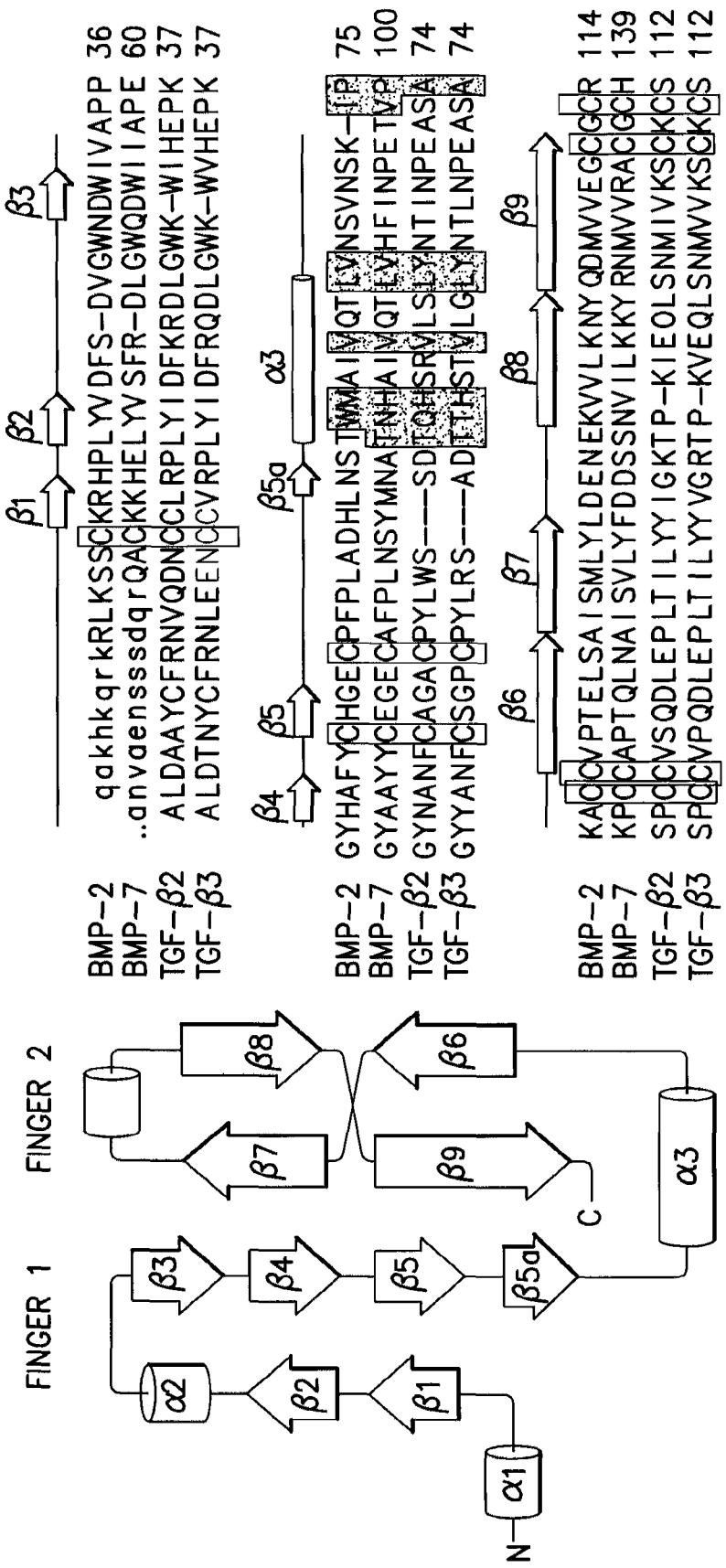
FIG. 1 shows a structural schematic diagram of human BMP2, BMP7 and TGF-β proteins and the total amino acid sequence thereof.
Figure 2:
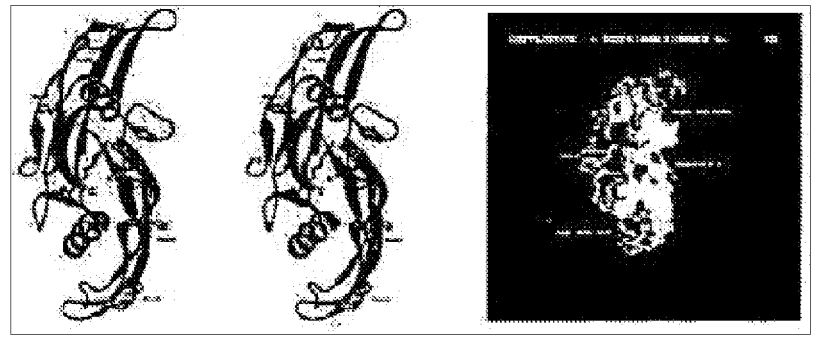
FIG. 2 is a photograph showing the two-dimensional and three-dimensional structures of previously commercially available rhBMP-2.

The non-activated TRPs according to the present invention have the biochemical structures and characteristics completely different from those of previously known active proteins, such as rhBMPs or TGF-β. Namely, the inventive non-activated TRPs have no biological activity by themselves before in vivo administration, whereas previously known rhBMPs and TGF-β proteins are in a biochemically activated state and have three-dimensional structures as shown in FIG. 1 and FIG. 2 (Eur. J. Biochem., 237:295, 1996; J. Mol. Biol., 287:103, 1999).

Thus, the preparation of prior activated rhBMPs and TGF-β has a common problem in that it should rely on the culturing of recombinant animal cells, having a significantly low productivity, such as CHO cells. In the case of rhBMP14 (MP-52) prepared by BioPharm, some of rhBMPs are prepared by the culturing of recombinant E. coli having high productivity than the animal cells, in which case many limitations are imposed on the biochemical structure of BMP to be prepared. Namely, active MP-52 may be prepared using the recombinant *E. coli*, but other kinds of active BMPs, such as rhBMP2, rhBMP4 and rhBMP7 or active TGF-β can not be prepared using the recombinant *E. coli*.

Meanwhile, US 2004/197867 A1 discloses a fusion polypeptide of a bone morphogenetic polypeptide and a protein transduction domain (PTD), and a method for inducing bone formation in animals by administering the fusion polypeptide. More specifically, said patent discloses that administering a fusion polypeptide of inexpensive LMP-1 (LIM mineralization protein-1) and PTD instead of directly administering expensive BMP induces the mRNA expression of BMP2 and BMP7, and also said patent mentions, as bone morphogenetic proteins, not only LMP but also BMP, TGF-β, SMAD, etc. However, it is well known that, even if mRNAs are formed in cells, proteins are not formed from numerous mRNAs due to the regulation and interference of mRNAs by micro RNAs (*Nature,* 409:363, 2001; *Cell,* 115:199, 2003). Therefore the contention that the increase of BMP mRNAs by LMP-1 is a critical factor for the differentiation of bone cells lacks credibility. In addition, even if PTD is used to introduce proteins into cells, it cannot be said that all the proteins are activated to show the expected bone morphogenetic potencies (*Curr. Protein Peptide Sci.,* 4:97, 2003). Particularly in the case of secretory proteins, such as BMPs, the pharmacological activities can be shown only through a series of complicated post-translational modification processes, unlike other kinds of proteins showing biomedical potencies of nuclear and cytoplasmic protein in the cells.

Particularly, the BMPs work by the pharmacological mechanisms and activation mechanisms completely different from those of LMPs which is probably a nuclear transcription factor. Therefore it is not predictable at all before appropriate experimental analyses that the simple replacement of LMP-1 with BMP can show the biomedical effects similar to those obtained from LMP-TAT. If PTD is used to introduce recombinant proteins into cells as in the case of US 2004/197867 A1, LMP-1 or SMAD may be activated to function as a gene regulatory factor, whereas BMP and TGA-β may show completely different behavior than from the case of LMP or SMAD. It is because the BMPs and TGF-β belong to secretory proteins, unlike LMPs (*Genes Dev.,* 15:2797, 2001; *J. Cell Biol.,* 144:139, 1999; *Curr. Prot. Pept. Sci.,* 4:97, 2003; *Nature,* 425:577, 2003). In other words, the BMPs and TGF-β proteins cannot show the expected biomedical potencies without highly complicated post-translational activation processes (e.g., intracellular processing and modification), unlike LMPs. Therefore it cannot be expected that, the PTD simply bound to BMPs would show the desired biological activities when it is administered in vivo. Unfortunately, the US 2004/197867 A1 does not mention any experimental evidence showing that bone formation is stimulated by the introduction of a fusion polypeptide of BMP and PTD. It does not rationalize either that the administration of BMP-PTD, instead of rhBMP, could provide any additional or differential effects than administration of prior rhBMPs.

The present inventors have found that the primary factor of the lack of efficiency in administering the previously known rhBMPs into living human beings or mammals is due to their biochemical activity and the three-dimensional steric structure. The production cost of the rhBMP becomes extremely high because of the biochemical activity of the BMPs. The low-productive animal cell culturing is preferred due to the activation of the BMPs. The separation, purification, storing, handling, and administration of the BMPs become inefficient and expensive, because the biological activity of BMPs is maintained even before administration.

Based on this finding, the present inventors first attempted to prepare a non-activated polypeptide showing no three-dimensional steroregularity at room temperature. Namely, in order to make the non-activated polypeptide to permeate cell membranes without cell membrane receptors, the non-activated polypeptides were fused with PTDs, such as TAT, and examined for permeation into cells. An inactivated BMP-TAT fusion polypeptide having no three-dimensional steric structure was prepared in this manner and was administered into cells. As shown by the Example 1 below, the fusion polypeptide of BMP-TAT, for example, easily permeate through the cell membranes, as expected, when administered into mammal cells. However, the permeated BMP-TAT does not show any biochemical activity, nor pharmacological efficacies associated with the stimulation of bone or cartilage formation or regeneration.

To additionally solve this problem, the present inventors have developed a practical method making the non-activated polypeptide to be activated, when administered into the human body, by proprotein convertase, such as furin, which is present in cells. Namely, we prepared a polypeptide (TRP) containing: PTD making the polypeptide to permeate cell membranes without cell membrane receptors of, e.g., human beings and mammals; FAD making the non-activated protein to be activated in cells by in vivo proprotein convertase, such as furin; and TRD being able to be activated to function to induce tissue growth or regeneration. The TRD can function to stimulate the formation or regeneration of bones or cartilages or improve the fibrosis and cirrhosis of kidneys, liver, lungs and heart, when permeated into animal cells by help of PTD and activated in vivo by the FAD. We have found that the above-prepared polypeptide not only permeates cell membranes but also is activated in vivo and then secreted to exhibit the effect of stimulating tissue growth or regenerating tissue.

The TRPs according to the present invention can be mass-produced in a practical manner through culturing bacteria, such as recombinant *E. coli*, without limitations caused by the biochemical structure of the proteins. They are maintained in a biochemically inactive state before in vivo administration. For this reason, their production cost is only a few tenths of the costs of previously known activated proteins (rhBMPs, TGF-β proteins, etc.) having uses similar thereto. The processes for separation, purification, handling, storage and administration of the present inventive TRPs are significantly simpler and more convenient than those of prior active rhBMP proteins.

Figure 3:
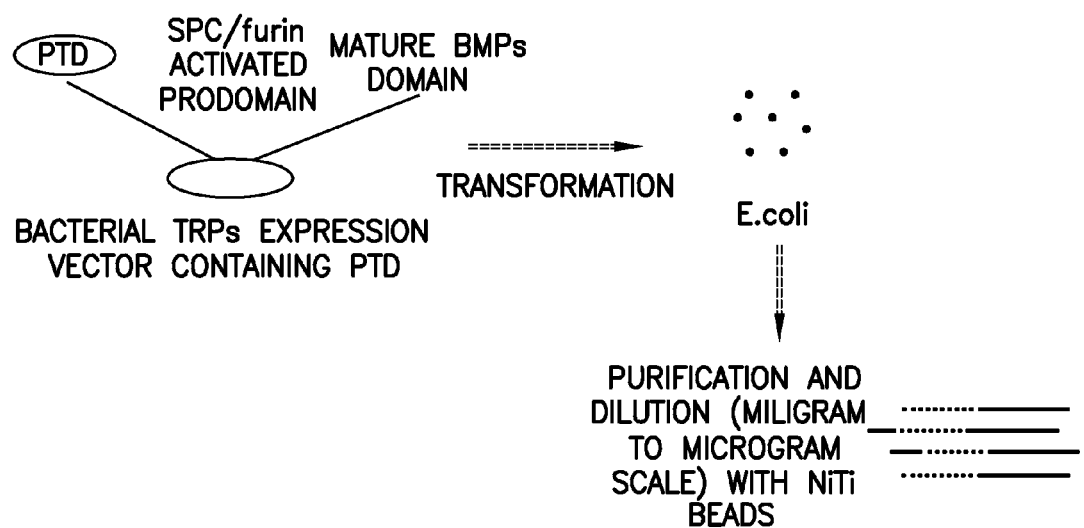
FIG. 3 shows a process for the preparation, separation and purification of TRP-1 according to the present invention.
Figure 4:
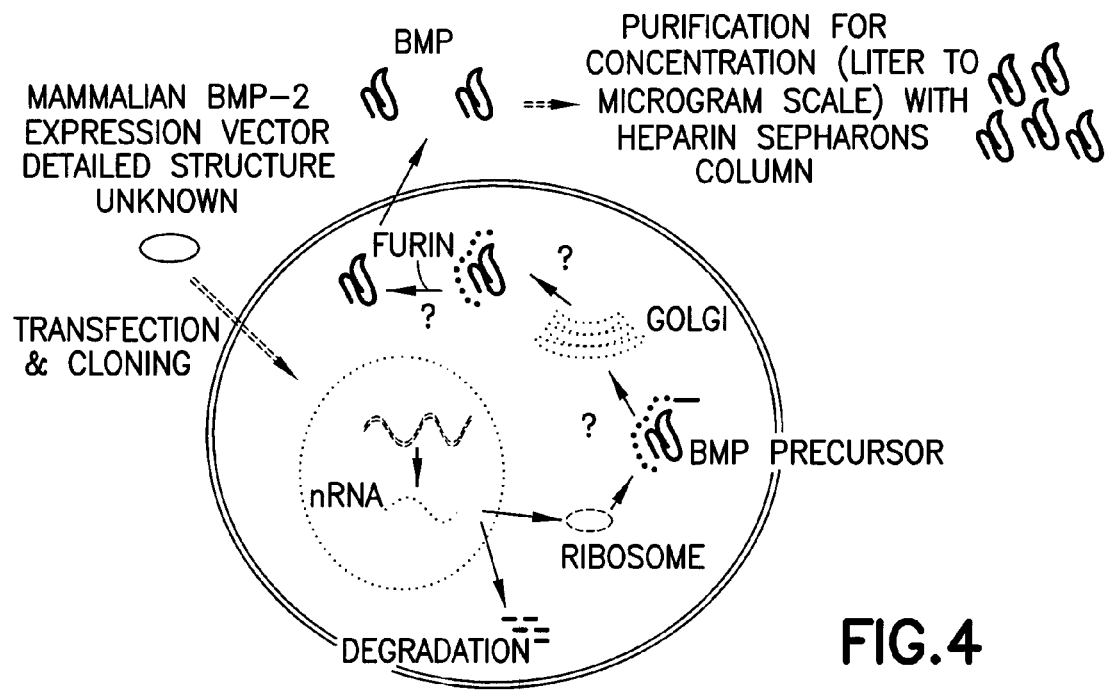
FIG. 4 shows a process for the preparation, separation and purification of the previously known rhBMP.

Unlike that the prior active BMPs had limitations on their preparation methods, the present invention has an advantage in that TRPs, which include BMPs and TGF-β proteins having various structures as TRDs, can be prepared using recombinant *E. coli* in a practical and inexpensive manner (see FIG. 3). FIG. 3 shows a process for separating and purifying TRP-1 according to the present invention, and FIG. 4 shows a process for separating and purifying rhBMPs according to the prior art (U.S. Pat. Nos. 4,968,590; 5,106,626; 5,106,748; 5,166,058; 5,187,076; 5,187,623; 5,208,219; 5,258,494; 5,266,683; 5,284,756; 5,399,346; and 6,593,109). As shown in the figures, the prior method includes a complicated separation and purification process and shows low purification yield because it comprises producing and secreting BMPs through the culture of transformed CHO cells. It shows very low purification yield to separate and to purify prior BMPs from a large culture medium by using herarin sepharous column, and the like. The inventive method has advantages in that it needs a very simple separation and purification process and in that it provides high purification yield. Namely TRP-1 according to the present invention is, unlike previously known rhBMP-2, in a non-activated state until administration into patients, and thus it does not require the culturing of a large amount of CHO cells. It is simple and easy to separate and purify the inventive TRP-1, and its purification yield is significantly higher than that of prior activated rhBMP-2. Accordingly, the non-activated TRPs according to the present invention have advantages in that they can be produced at the cost of a few tenths of that of the prior commercially available rhBMP-2, and in that it is convenient to store and administer the inventive TRPs.

The present invention fundamentally solves the high-cost problem possessed in common by the previously known rhBMPs, and the inefficiency problems associated with the processes of separation, purification, storage and administration of the active rhBMP products. Also, it was found that the non-activated polypeptides have new pharmacological mechanisms completely different from those of the prior rhBMPs, when administered directly into living human beings or mammals. The inventive TRPs show equal or better biomedical efficacies on the stimulation of tissue formation or the regeneration of tissue comparing with the previously known rhBMPs or TGF-β.

Figure 5:
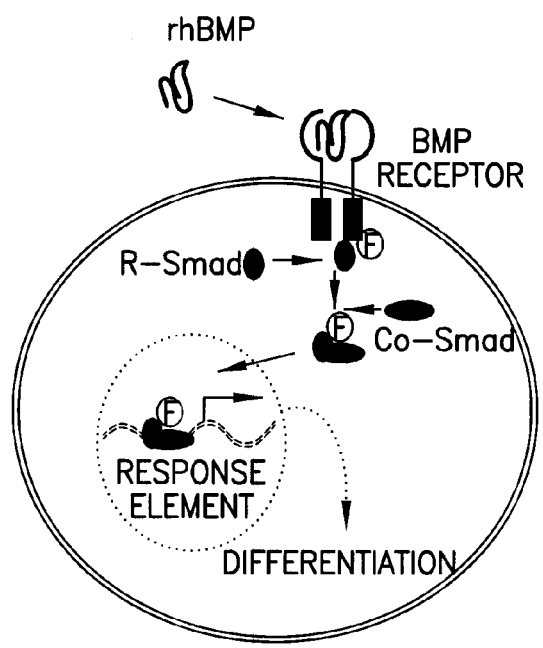
FIG. 5 shows the pharmacological mechanism of the previous rhBMP.
Figure 6:
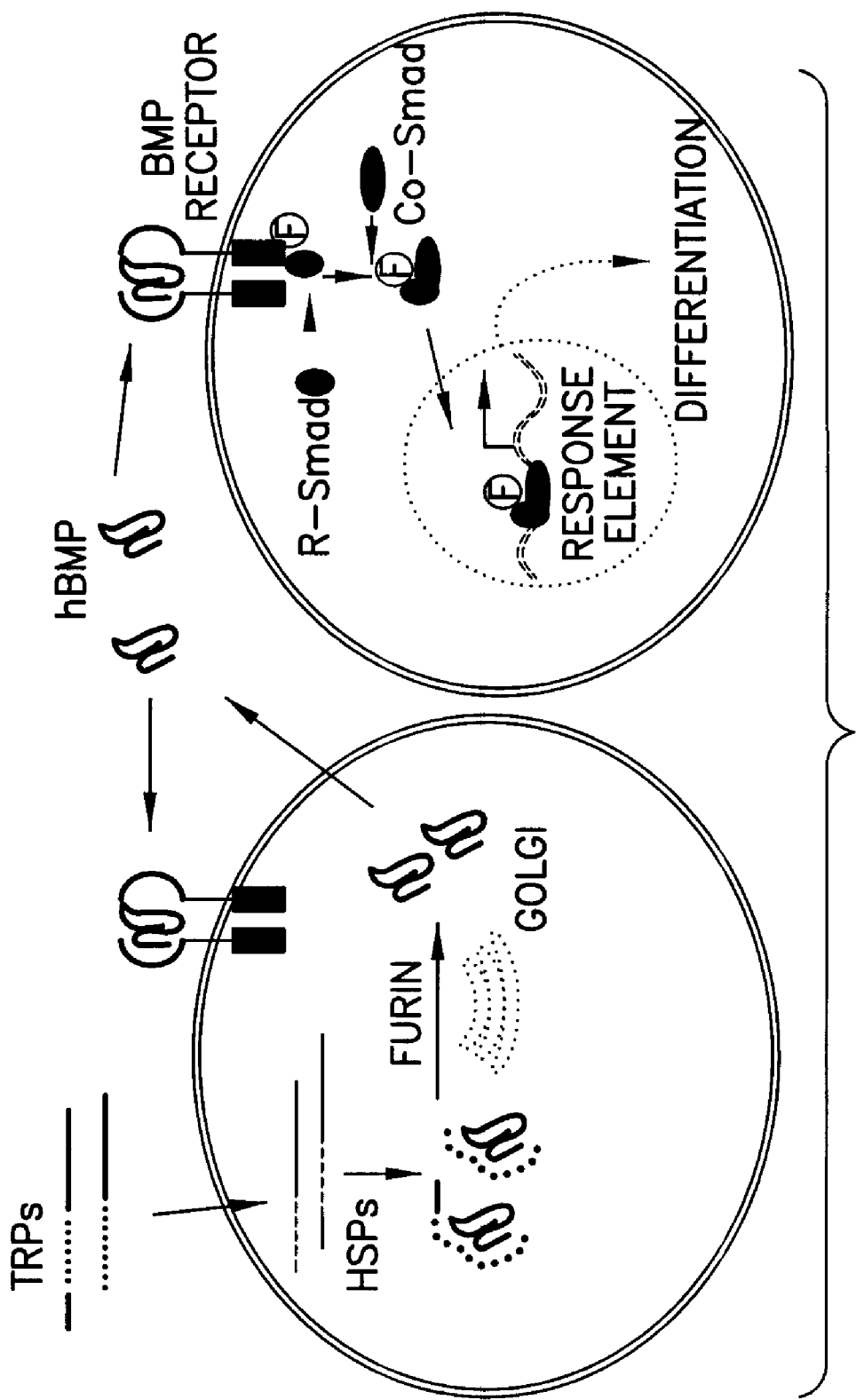
FIG. 6 shows the pharmacological mechanisms of the non-activated TRPs prepared according to the present invention.

The non-activated TRPs according to the present invention have pharmacological mechanisms completely different from those of the previously known active rhBMPs, TGF-β, and the like. That is, when the non-activated TRPs according to the present invention are administered in vivo to human beings or mammals, they can stimulate the formation of bones or cartilages or improve the fibrosis or cirrhosis of kidneys, liver, lungs and heart, according to pharmacological mechanisms completely different from those of previously known rhBMPs or TGF-β proteins. For example, the prior rhBMPs, as shown in FIG. 5, bind to native receptors from cells and induce the differentiation of bone formation cells through the Smad signaling pathway, whereas the inventive TRPs, as shown in FIG. 6, permeate the cell membranes independently of the receptors and are restructured by HSP, etc., in cells, and the restructured TRPs are cleaved and activated by proprotein convertase, such as furin, which is present in golgi complexes and endosomes, and the activated BMPs are secreted out of the cells, and the secreted BMPs bind to the receptor of autocrine or paracrine cells to induce the differentiation of bone formation cells.

Also, the present invention adopts a therapeutic method completely different from the prior method attempted to induce bone formation. Namely, according to the present invention, a non-activated polypeptide (TRP) consisting of PTD, FAD and TRD is prepared in recombinant bacteria, and the prepared polypeptide is administered to human patients or mammals. The TRP is refolded in cells in vivo by HSP (heat shock protein), etc. and is cleaved by furin, etc., so as to be refolded to an activated BMP, which is then secreted extracellularly so as to induce bone formation.

The TRPs according to the present invention are polypeptides containing: PTD making the polypeptide to permeate a cell membrane without cell membrane receptors; FAD having at least one proprotein convertase cleavage site and making non-activated TRD to be activated in cells by cleavage with the proprotein convertase; and non-activated TRD which can be activated in cells by the proprotein convertase cleavage of the FAD and which can stimulate tissue growth, formation or regeneration. The inventive TRPs are inactive by themselves, but after permeation into organisms or cells, the FAD is cleaved by proprotein convertase found in most cells at large amounts so as to activate the TRD, and the activated protein is secreted extracellularly to exhibit tissue regeneration potencies. These TRPs according to the present invention can solve all the problems of the previously known active proteins that are expensive to be produced, not easy to be stored and handled.

In the present invention, a recombinant vector was first prepared by inserting the base sequence of a BMP pro-domain having a furin cleavage site and the base sequence of PTD in front of the 5' region of a BMP gene, and inserting in front thereof a base sequence for tagging, at least four histidine-encoding base sequences for separation and purification, and ATG as an initiation base sequence.

In the present invention, as the BMP gene, a gene encoding hBMP2 set forth in SEQ ID NO: 1 or hBMP7 set forth in SEQ ID NO: 6 was used but not limited thereto. Also, as the FAD, an hBMP2 pro-domain set forth in SEQ ID NO: 14 or an hBMP7 pro-domain set forth in SEQ ID NO: 19 was used but not limited thereto. For example, the pro-domains of other BMPs and TGF-β proteins may also be used without limitations if they have a proprotein convertase cleavage site, such as furin, and can be cleaved by proprotein convertase in cells to activate TRD.

Also, as a PTD, TAT (YGRKKRRQRRR: SEQ ID NO: 27) was used in the present invention but is not limited thereto. For example, PTDs, such as *drosophila melanogaster*-derived Antp peptide, VP22 peptide (Gene Therapy, 8:1, Blackbirch Press, 2001) and mph-1-btm (US 2005/0147971 A1), may also be used. Also, as a tagging base sequence, an X-press tag was used, but Flag, Myc, Ha, GST, etc., may also be used.

To construct the recombinant vector, pRSET, which is resistant to ampicillin and commercially available, was used in the present invention but is not limited thereto. For example, a bacterial vector having kanamycin as selective marker, a mammalian cell expression vector, such as pcDNA, and viral vectors, such as pPGS and pBabe, may also be used.

Then, microorganisms transformed with the recombinant vector were cultured to express the inventive TRPs, and the expressed TRPs were separated and purified. In the present invention, the transformed *E. coli* may be cultured in a generally used medium, and IPTG is preferably added in order to induce the over-expression of the fusion polypeptides.

In the present invention, although *E. coli* was used as the transformed microorganisms, it is possible to use other kinds of bacteria, yeasts or molds. Furthermore, only active sites may also be chemically synthesized and used without using microorganisms.

The fusion polypeptides expressed by the culture of the transformed microorganisms can be isolated using a GST-fusion protein or other conventional methods for protein separation and purification. For example, the TRPs according to the present invention may be purified through inducing the precipitation of the proteins using the concentration gradient of urea or ammonium sulfate and dialyzing the precipitates to remove salts. Also, because the present invention does not require the two-dimensional or three-dimensional structure of the over-expressed polypeptides, it is preferable that the proteins having a two-dimensional or three-dimensional structure are converted to one-dimensional linear structure.

When the inventive TRPs are administered into, e.g., bone cells, progenitor cells and stem cells, the FAD of the TRPs are cleaved by proprotein convertase, such as furin, to activate TRDs (e.g., BMP), which are then secreted. In other words, the TRPs permeated into cells specifically bind to F-actin in the cells, and recover a three-dimensional structure by factors, such as HSP70, and their furin cleavage sites are cleaved by furin, which is an intracellular cleavage enzyme, to activate TRDs (e.g., BMPs), which are then secreted extracellularly. The inventive TRPs introduced into cells have a half-life of 3-24 hours depending on the type and activity of the cells, indicating that the permeated proteins have activation time which varies depending on the type of cells.

Meanwhile, when the furin cleavage sites were mutated, activated BMPs were not secreted. This suggests that the protein modification by the furin cleavage enzyme is critical to the intracellular processing and activation of the permeated proteins. Also, when hBMP is naturally synthesized and processed in vivo, a signal peptide is known to play an important role in the intracellular and activation of proteins. However, even when the signal peptide was deleted in the present invention, the resulting BMP showed effects similar or better than those of wild-type BMP2 in bone formation. This suggests that the transfer of the inventive BMP using TAT and FAD does not require the signal peptide unlike the natural hBMP in vivo.

When the inventive TRPs are administered to cells at a concentration of more than 0.1 nM, the TRPs transduce into the cells in a concentration-dependent manner and converted into activated BMPs in the cells, and the activated BMPs are secreted out of the cells. The inventive TRPs directly permeated the cell membrane within one hour independently of a BMP receptor present in the cell membrane, and the cell membrane permeation process was found to be temperature-independent, indicating that the permeation process does not require the cell membrane receptor. Also, even when various concentrations of TRPs were administered to cells, cytotoxicity was not observed.

As a result, the inventive non-activated TRPs do not need to be maintained in three-dimensional structures, unlike previously known active BMPs, and they permeate bone cells in the form of a one-dimensional linear structure and are converted to active BMPs, and then are secreted out of cells and show tissue regenerative potencies. While the prior hBMPs directly show bone morphogenetic potencies, the inventive TRPs show tissue regenerative potencies through indirect activation in vivo. Thus, the inventive non-activated TRPs do not require additional equipment or cost for maintaining a three-dimensional structure, and it is very easy to separate and purify them. Also, the TRPs are produced in simple processes at a low cost, and they provide increased medical efficiency. These advantages suggest that the inventive TRPs can solve all the problems of the prior rhBMP proteins. The characteristics of the inventive TRPs are shown in Table 1 below in comparison with the prior activated rhBMP2 and rhBMP7 proteins. Table 1 shows the characteristics of processes for the separation, purification, storage and administration of the inventive TRP products in comparison with those of the previously known activated rhBMPs.

TABLE 1

| Items | Prior bone morphogenetic proteins (rhBMP-2 or rhBMP7) | Inventive fusion polypeptides (TRPs) |
|---|---|---|
| Production method | Culture transformed CHO cells | Culture transformed E. Coli |
|  | Produce while maintaining transformed CHO cells | Maintain transformed E. coli in a simple manner |
|  | Separate from large cell medium, and concentrate | Separate directly from E. coli, and dilute |
| Production cost | Very high | Significantly lower than those of the prior art |
| Production equipment and facilities | Require large-scale equipment and facilities | Very simple |
| Products | Activated rhBMP2, rhBMP7 | Fusion polypeptides of PTD-FAD-TRD |
| Three-dimensional structure | Active three-dimensional structure (FIG. 1 and FIG. 2) | Non-activated peptides |
|  | Naturally occurring structure | Naturally non-occurring random structure |
| Solubility in cleaning material and physiological saline | Soluble; Loss of three-dimensional structure and activity | Insoluble; No effect on structure and activity |
| Need of carrier for administration in vivo | Diffuse rapidly due to water-solubility. Need suitable carrier for local administration | Are insoluble and transducer rapidly into adjacent cells. No need carrier for local administration |
| Stability of storage | Loss of activity upon breakdown of three-dimensional structure; Not storable above 37° C.; low stability of storage | Independent on structure; Storable above 37° C.; Good stability of storage |
| Biological mechanism | Directly bind to cell membrane receptors (direct action) | Activated proteins are secreted out of cells (indirect action) |
| Intracellular specific structure binding to protein after administration | No relevant data | F-actin |
| Intracellular processing | No relevant data | Activation by cleavage with furin enzyme |
| Temperature dependency in administration | Needs live body temperature to be bound to receptors | Permeate all living cells independently of temperature |
| Half time for activation | No relevant data | 3-12 hours |
| Cytotoxicity | No cytotoxicity at 200 nM concentration | |
| Funtion of signal peptide in process for protein activation | Necessary | Not necessary |

TABLE 1-continued

| Items | Prior bone morphogenetic proteins (rhBMP-2 or rhBMP7) | Inventive fusion polypeptides (TRPs) |
|---|---|---|
| Cell selectivity | Signal only through BMP receptors | Permeable all kinds of cells without help from receptors |
| Medical potency | | Similar |
| Administration mode | | Same |

The inventive non-activated TRPs shall be useful for the treatment of bone diseases. For example, the TRPs can either induce the growth of bones in an environment where bones are not normally formed, or improve bone resorption by bone fracture resulting from external injury, or stimulate the fixation of artificial joints. Specifically, the inventive TRPs shall be used for the treatment of congenital anomaly, tumor excision and reconstruction, craniomaxillofacial deformity, periodontal disease, etc., to provide an environment for inducing the differentiation of bone formation cells or stimulating the growth of bone formation cells. In addition, the TRPs according to the present invention can be used to prevent the fibrosis of tissues, such as kidneys or liver, and to induce the regeneration of tissues, and may also be used for other applications, such as the regeneration of nerves or blood vessels.

The non-activated TRPs according to the present invention can be used by themselves or in the form of pharmaceutically acceptable acid-added salts or metal complexes, for example, of zinc or iron salts. Preferable examples of the acid-added salts, which can be used in the present invention, include hydrogen chloride, hydrogen bromide, sulfate, phosphate, maleate, acetate, citrate, benzoate, succinate, malate, ascorbate, and tartarate.

The inventive composition containing the non-activated TRP as an active ingredient is preferably prepared by mixing and diluting the active ingredient with a pharmaceutically acceptable excipient or matrix carrier or by sealing the active ingredient into a receptacle-like carrier, depending on administration routes and modes and intended therapeutic uses. Moreover, the inventive composition may also be used in combination with other drugs useful for the treatment of bone defects. In this case, the preparation of a physiologically acceptable composition having the desired pH, isotonicity and stability may be performed using any conventional method known in the art to which the present invention pertains. The matrix used in the present invention may be selected depending on bioadhesion, biodegradability, mechanical properties, attractive appearance and contact properties. Examples of the carriers, which can be used in the present invention, include biodegradable and chemical substances, such as calcium sulfate, tricalcium phosphate, hydroxyapatite and polylactic acid; biodegradable and biological substances, such as bone or skin collagens, and other pure proteins or cellular matrix components; non-biodegradable and chemical substances, such as sintered hydroxyapatite, bioglass, aluminate and other ceramics; combinations of the above substances, such as polylactic acid, hydroxyapatite, collagen and tricalcium phosphate. However, the present invention is not limited to the above-mentioned carriers.

Examples of excipients, which can be used in the present invention, include lactose, dextrose, sucrose, sorbitol, mannitol, calcium silicate, cellulose, methylcellulose, microcrystalline cellulose, magnesium stearate, polyvinylpyrrolidone, water, methylhydroxybenzoate, propylhydroxybenzoate, talc, and mineral oil.

Meanwhile, the composition containing the non-activated TRP according to the present invention is preferably used in the form of an injection solution or capsule in order for the composition to be introduced into bone defect sites. The dose of the inventive composition can be determined considering the kind of excipients or matrix carriers used, the weight of formed bones, bone injury sites and the condition of injured bones in patients, the patient's age, sex and diet, disease severity, administration period, and other clinical factors. Thus, for example, a conventionally known effective amount of the composition may be administered at one time or in portions, considering the weight of bones, and additional administration can be determined while the growth of bones is observed.

EXAMPLES

Hereinafter, the present invention will be described in more detail by examples. However, it will be obvious to those skilled in the art that the present invention is not limited by these examples, and various variations and modifications to theses examples are possible without deviating from the sprit and scope of the present invention.

Particularly, although the following examples illustrated only hBMP2 and hBMP7 as TRDs contained in TRPs, those skilled in the art will appreciate that it is possible to use not only human BMPs, such as hBMP3, hBMP4, hBMP6, and hBMP14 (MP-52), but also BMPs derived from mammals, such as rats, cattle, pigs, and other animals. Furthermore, those skilled in the art will appreciate that it is possible to use, in addition to BMPs, other kinds of polypeptides, such as a group of TNF-β proteins, including TGF-β, β-NGF (β-nerve growth factor), β-amyloid, ADAMs (a disintergrin and metalloproteinase-like), and ectodysplasin-A (Eda-1), a group of MMPs, including MT1-MMP (membrane type-matrix metalloproteinase) and MMP-2, and insulin-like growth factor-1 (IGF-1).

Moreover, although the following examples illustrated only the pro-domains of BMPs, as FADs contained in TRPs, those skilled in the art will appreciate that any pro-domain may be used without limitations if it has a proprotein convertase cleavage site and is cleaved by proprotein convertage in cells to activate TRDs.

Example 1

Preparation of [TAT-hBMP2] Fusion Polypeptide

Each of proteins belonging to a BMP/TGF-β group consists of a dimer comprising the same two peptides linked to each other by one disulfide bond. In this regard, each of the peptides consists of 120-140 amino acids depending on the type of BMPs, one of 7 cystein terminal groups present in BMPs forms a disulfide bond with the same site of the other peptides to form a dimer, and the remaining 6 cysteins form 3 intrachain disulfide bonds in the same amino acids, resulting in a unique three-dimensional structure (*Proc. Natl. Acad. Sci.*, 93:878, 1996; *J. Bone Joint Surg.*, 83:S1, 2001). Herein, BMP2 (SEQ ID NO: 1) consists of 114 amino acids, BMP7

(SEQ ID NO: 40) consists of 139 amino acids, and each of TGF-β2 (SEQ ID NO: 41) and TGF-β3 (SEQ ID NO: 42) consists of 112 amino acids. FIG. 1 shows the amino acid sequences of these peptides and a schematic diagram of the three-dimensional structure thereof, and FIG. 2 shows the three-dimensional structure of previously known BMP2 (*Eur. J. Biochem.*, 237:295, 1996; *J. Mol. Biol.*, 287:103, 1999). The locations of the seven cysteines in BMP/TGF-β are all conserved, suggesting that the cysteins play an important role in the three-dimensional structure.

Accordingly, as well known in the art, when a fusion protein prepared by binding PTD to the previously known hBMP2 is introduced into cells, it is expected that this fusion protein will permeate the cell membrane even without the cell membrane receptor so that it will be refolded into a biologically active protein by, e.g., HSPs (heat shock proteins) (*Nature Med.*, 4:1449, 1998; *Science*, 285:1569, 1999).

For this reason, in this Example, a gene encoding hBMP2 having an amino acid sequence of SEQ ID NO: 1 was amplified by RT-PCR using the total mRNA of Saos-2 cells (American Type Culture Collection, ATCC HTB-85) as a template with primers of SEQ ID NOs: 28 and 29. For cloning into a bacterial expression vector, a restriction enzyme Kpn I site (5'-ggtacc-3') was added to the 5' region of each of the primers. Cloning primers used in Examples below also contained the restriction enzyme Kpn I site.

```
SEQ ID NO: 28:
5'-caa gcc aaa cac aaa cag cgg aaa-3'

SEQ ID NO: 29:
5'-ttt gct gta cta gcg aca ccc aca-3'
```

Figure 7:
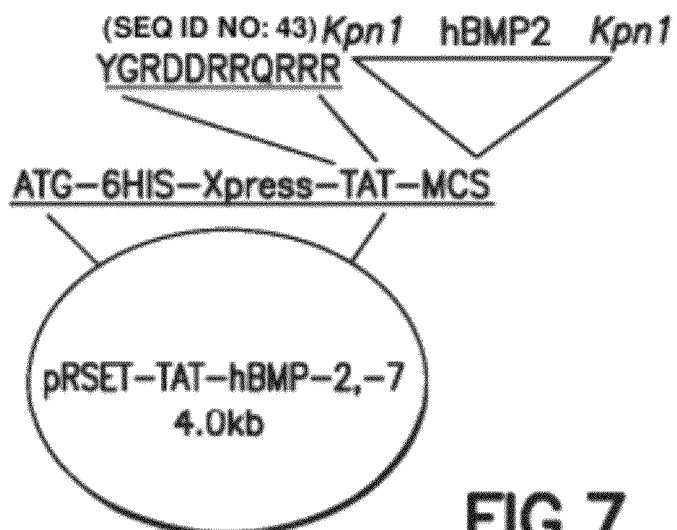
FIG. 7 shows a recombinant expression vector having TAT bound to an hBMP2 gene.

The amplified hBMP2 gene was inserted into a TA cloning vector (Invitrogen, Inc). It was confirmed that the 114 amino acids are contained by comparison with a base sequence (NCBI, NM_001200) in GenBank. The cloned hBMP2 gene was subcloned again into the KpnI sites of a pRSET bacterial expression vector (Invitrogen, Inc), the base sequence of TAT (YGRKKRRQRRR: SEQ ID NO: 27) was inserted in the 5' region of the hBMP2 gene. Then, in front thereof, an X-press (Invitrogen, Inc) tag, six histidine-encoding base sequences for separation and purification, and initiation base sequence ATG, were inserted, thus constructing a recombinant expression vector for the expression of BMP2 (see FIG. 7). As a negative control, a vector inserted with no TAT was used.

The constructed recombinant vector was introduced into *E. coli* BL21 (Invitrogen Inc.) by a conventional heat shock method, and cultured at 37° C. for 2-3 hours. To the culture medium, 1 mM of IPTG (isopropylthio-galactoside) was added, and the resulting culture medium was additionally cultured for 2-18 hours to induce the expression of TAT-BMP2.

The culture broth was centrifuged and then the cell pellet was collected. 8M of a urea solution was added into the cell pellet to remove the two-dimensional and three-dimensional structures of BMP. Ni—Ti beads (Qiagen) were added thereto so as to bind the TAT-BMP2 to the beads, after which the beads were washed three times with the same solution and eluted using imidazole and high-salt buffer, thus obtaining a purified TAT-BMP2.

Figure 8:
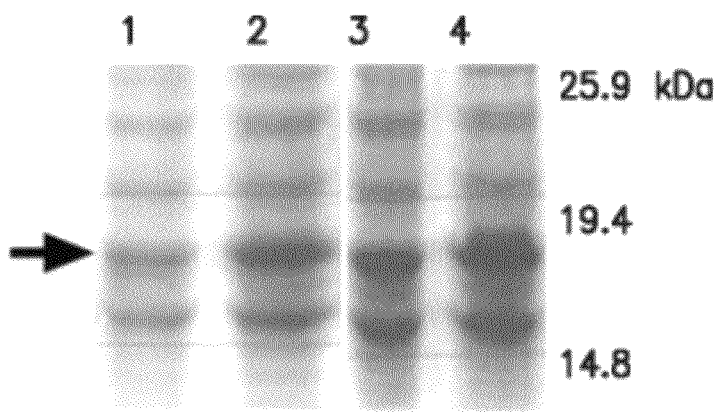
FIG. 8 shows electrophoresis photographs of a total protein before and after inducing protein expression by IPTG during the culture of E. coli transformed with the recombinant expression vector shown in FIG. 7.

FIG. 8 shows the results of electrophoresis for the total protein before and after inducing protein expression by IPTG during the culture of the transformed *E. coli* BL21. In FIG. 8, the arrow represents the TAT-BMP fusion protein induced by IPTG, lane 1 represents uninduced TAT-BMP2, lane 2 represents TAT-BMP2 induced by IPTG, lane 3 represents uninduced BMP2 (w/o TAT), and lane 4 represents BMP2 (w/o TAT) induced by IPTG. As shown in FIG. 8, in the case where the production of the fusion proteins was induced by the addition of IPTG, the TAT-BMP2 fusion protein was produced in a large amount compared to the control group.

Figure 9:
FIG. 9 shows the results of Western blot analysis for TAT-BMP2 using an anti-X-press antibody.

FIG. 9 shows the results of Western blot analysis using an anti-X-press antibody for the purified TAT-BMP2 and BMP2 (w/o TAT). In FIG. 9, lanes 1 and 2 represent TAT-BMP2 and BMP2 (w/o TAT), respectively. As shown in FIG. 9, the addition of TAT (~20 kDa) resulted in a slight increase in molecular weight compared to the case of no TAT addition (~18 kDa). These results suggest that the TAT-hBMP2 fusion polypeptide was successfully prepared.

Figure 10:
FIG. 10 is a Western blot photograph showing that TAT-BMP2 permeates cell membranes to transduce into the cells.

In order to examine whether the prepared TAT-BMP2 permeates the cell membrane, primarily cultured gingival fibroblasts were treated with the TAT-BMP2 at a concentration of 4 nM for 2 hours, and the cells were collected and Western-blotted with an anti-X-press primary antibody (Invitrogen, Inc). As a result, as shown in FIG. 10, the TAT-BMP2 mostly permeated the cell membrane within 2 hours, and the peptide having no TAT did not permeate the cell membrane. Lane 1 shows the result of Western blot for 4 nM of the TAT-free BMP2 treated for 2 hours, and lanes 2 through 6 show the results of Western blot using an anti-X-press antibody for the intracellular expression of the same concentration of TAT-BMP2 proteins treated for 0 hr, 15 min, 30 min, 1 hr and 2 hr, respectively. Lane 7 is a Western blot positive control analyzed using 10 ng of TAT-BMP2.

Figure 11:
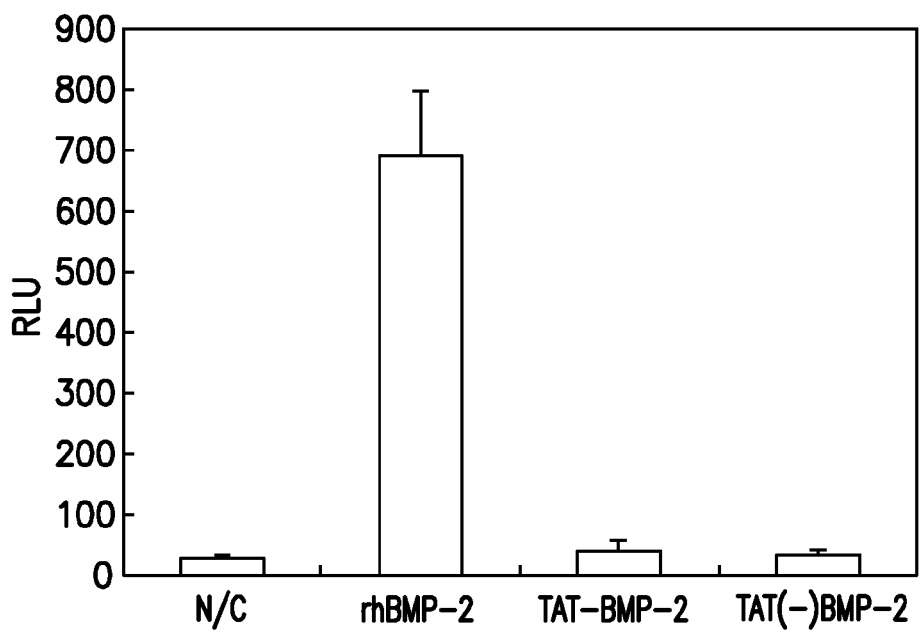
FIG. 11 is a photograph showing the alkaline phosphatase (ALP) activity of TAT-BMP2.
Figure 12:
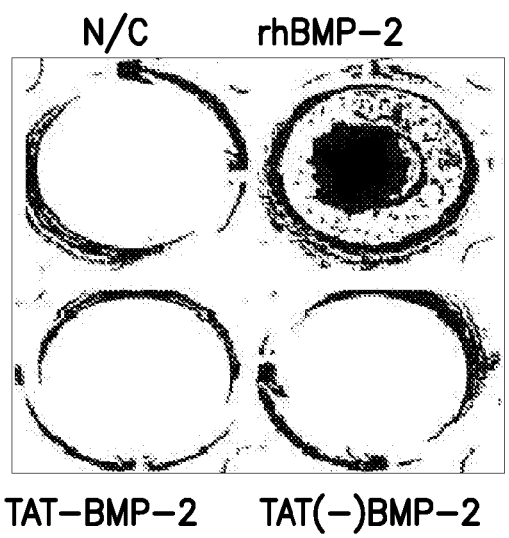
FIG. 12 is a photograph showing that fibroblasts treated with TAT-BMP2 and commercially available rhBMP-2 were subjected to von Kossa staining to examine the differentiation of bone cells and the formation of mineralized substances.

In order to examine whether TAT-BMP2 introduced into cells is refolded to biologically active BMP2 proteins, which then induce the differentiation of bone cells, 2 nM of TAT-BMP2 was administered to the same cells at 48-hr intervals, and after one week, the cells were measured for alkaline phosphatase (ALP) activity. After culturing for 2 weeks, the cells were subjected to von Kossa staining to observe the formation of mineralized substances. As a negative control, TAT-free BMP2 was used, and as a positive control, commercially available rhBMP-2 was used. FIG. 11 shows ALP activities. In FIG. 11, the negative control (N/C) is a result for primarily cultured fibroblasts treated only with a medium for one week, rhBMP-2 is a result for cells treated with commercially available BMP2 at a concentration of 2 nM for one week, TAT-BMP-2 is a result for cells treated with TAT-BMP-2 of this Example at a concentration of 2 nM for one week, and TAT(-)BMP-2 is a result for cells having TAT deleted from TAT-BMP-2. FIG. 12 shows the results of von Kossa staining conducted to observe the deposition of mineralized substances. As shown in FIG. 11 and FIG. 12, the TAT-hBMP-2 of this Example had no biological activity, unlike commercially available rhBMP-2.

Example 2

Preparation of [TAT-FAD-hBMP2] Fusion Polypeptide (TRP-1)

As described in Example 1, hBMP2 shows biological activity by forming a characteristic internal three-dimensional structure and a dimer by a disulfide bond. However, as described in Example 1, a fusion protein of TAT and hBMP2 had no biological activity to induce bone cell differentiation even though it successfully permeated the cell membrane. This means that proteins having biological activity by secretion are insufficient to show activity only with the restructuring of amino acids by, e.g., HSPs, unlike the prior PTD-fused proteins (*Trends Cell Biol.*, 10:290, 2000; *Curr. Prot. Pept. Sci.*, 4:97, 2003).

BMPs and TGF-β are present in a form of precursor consisting of more than 400 amino acids, when biosynthesized in intracellular ribosomes. The synthesized amino acids transport to Golgi complexes, endosomes, etc., by signal peptides present in the N-terminal region, and cleaved and activated by proprotein convertase, such as furin, and then secreted extracellularly (*Nature Rev. Mol. Cell. Biol.*, 3:753, 2002; *J. Cell Biol.*, 144:139, 1999). The proteins are subjected to post-translational modification in the golgi complexes, etc., in which a signal peptide and prodomain located at the amino N-terminal region play a critical role (*Mol. Biol. Cell*, 15:5012, 2004). In this process, the BMP precursor is activated into a mature BMP moiety by the cleavage of the furin cleavage site (-RSKR-) with furin and then secreted, similarly to other secretory proteins (Constam, D. B. & Robertson, E. J., *J. Cell Biol.*, 144:139, 1999; Cui, Y. et al., *Genes & Development*, 15:2797, 2001). However, in said article, there is neither mention of a method for the intracellular administration of the BMP precursor, nor suggestion that the BMP precursor is introduced into cells in the form of a fusion with, particularly PTD.

Those known proprotein convertases, such as furin, include PC7, PC5/6A, PC5/6B, PACE4, PC1/3, PC2, and PC4 (*Nature Rev. Mol. Cell. Biol.*, 3:753, 2002). They are abundantly found in most of intracellular organelles, particularly Golgi networks, endosomes, and secretory granules, and play important roles not only in the activation of various proteins, but also in the activation of infectious diseases. Human mature proteins, which are activated by proprotein convertase, such as furin, include, in addition to BMPs/TGF-β, a group of TNF-α proteins, such as β-NGF (β-nerve growth factor), β-amyloid, ADAMs (a disintergrin and metalloproteinase-like) and ectodysplasin-A(Eda-1), a group of MMPs, including MT1-MMP (membrane type-matrix metalloproteinase) and MMP-2, and IGF-1 (*Nature Rev. Mol. Cell. Biol.*, 3:753, 2002).

It is particularly known that, when BMPs are naturally biosynthesized in cells, one or two furin cleavage sites in the prodomain of the BMP precursor contribute to the activation of BMPs (*J. Cell Biol.*, 144:139, 1999; *Genes Dev.*, 15:2797, 2001). In the case of human BMP2, one or two furin cleavage sites (RXKR, wherein R: Arg, K: Lys, X: other amino acids except for basic amino acids) are present in the prodomain and were deduced to play an important role in the activation and secretion of the PTD-BMP2 fusion protein. To prove this hypothesis, in this Example, a polypeptide having a structure of TAT-FAD-hBMP2 was prepared by adding a furin cleavage site-containing FAD having an amino acid sequence of SEQ ID NO: 14 to the TAT-hBMP2 of Example 1.

For this purpose, to add the FAD-encoding base sequence, DNA having both a base sequence encoding hBMP2 of SEQ ID NO: 1 and a base sequence encoding FAD having an amino acid sequence of SEQ ID NO: 14 was amplified in the same manner as in Example 1 using primers of SEQ ID NOs: 30 and 31. The base sequence of the amplified DNA was confirmed and then, the gene was cloned into a bacterial expression vector in the same manner as in Example 1.

```
SEQ ID NO: 30:
5'-gag ttt ttc cat gtg gac gct ctt-3'

SEQ ID NO: 31:
5-'ttt gct gta cta gcg aca ccc aca-3'
```

The transformed *E. coli* was cultured and purified in the same manner as in Example 1, thus obtaining TAT-FAD-hBMP2 (TRP-1). Namely, the culture broth having TRP-1 produced in *E. coli* was centrifuged, and to the supernatant and cell pellet, 8M of urea solution was added to remove the two-dimensional and three-dimensional structures of BMP2. To the remaining substance, Ni—Ti beads (Qiagen) were added so as to bind TRP-1 to the beads, and the beads were washed three times with the same solution and eluted using imidazole and high-salt buffer, thus obtaining a purified TRP-1 (see FIG. 3).

Figure 13:
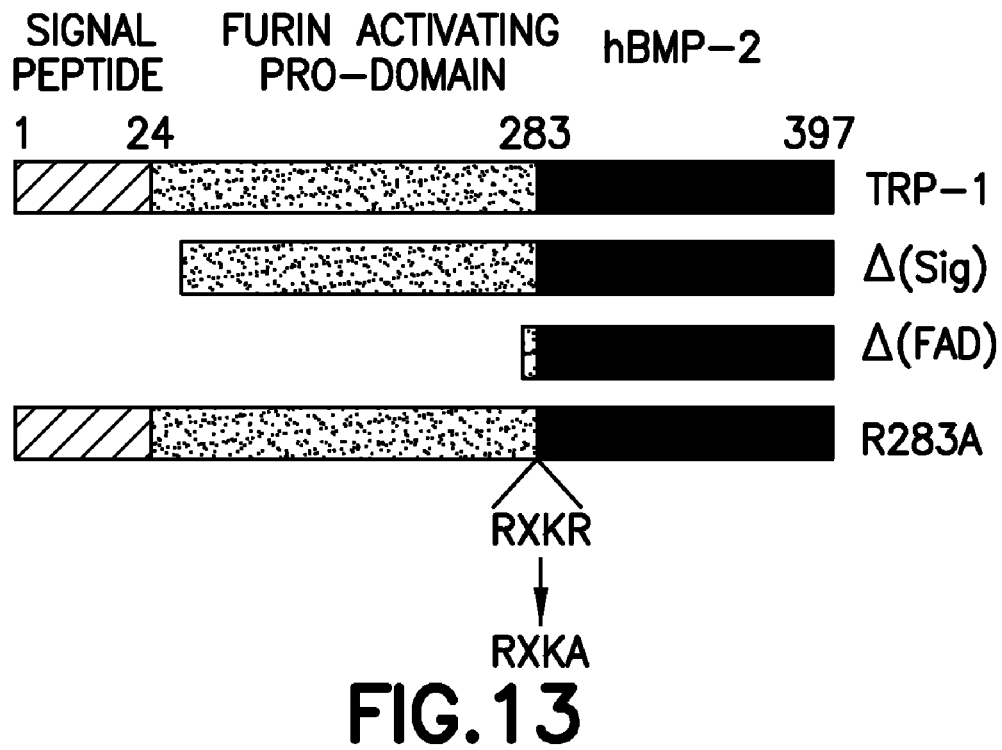
FIG. 13 is a schematic diagram of TRP-1 variant designed to examine a furin activation mechanism, which shows that a signal peptide, expected to regulate the post-translational modification, and a pro-domain, activated by furin, are bound to BMP2.

Meanwhile, to confirm the importance of the signal peptide, the prodomain and the furin cleavage site, the constructed expression vector as a template and each of primers of SEQ ID NOs: 32 and 33 (ΔSig), SEQ ID NOs: 34 and 35 (ΔPro), and SEQ ID NOs: 36 and 37 (R283A), were used to construct the respective deletion or mutation vectors. A schematic diagram of these vectors is shown in FIG. 13.

```
SEQ ID NO: 32:
5'-tcc acc atg gcc ggt acc ctc gtt ccg gag ctg
ggc-3'

SEQ ID NO: 33:
5'-gcc cag ctc cgg aac gag ggt acc ggc cat ggt
gga-3'

SEQ ID NO: 34:
5'-tcc acc atg gcc ggt acc gat gga aaa ggg cat
cct-3'

SEQ ID NO: 35:
5'-agg atg ccc ttt tcc atc ggt acc ggc cat ggt
gga-3'

SEQ ID NO: 36:
5'-ctc cac aaa aga gaa aaa gct caa gcc aaa cac
aaa cag-3'

SEQ ID NO: 37:
5'-ctg ttt gtg ttt ggc ttg agc ttt ttc tct ttt
gtg gag-3'
```

*E. coli* was transformed with each of the constructed expression vectors and then cultured and purified in the same manner as described for TRP-1, thus obtaining several TRP-1 variants. In FIG. 13, TRP-1 represents TAT-FAD-hBMP2 according to this Example, which comprises FAD added to TAT-hBMP2; Δ(Sig), was obtained by deleting a signal peptide portion (amino acid residues 1-24 of SEQ ID NO: 14) from TAT-FAD-hBMP2; Δ(FAD) was obtained by deleting an N-terminal FAD (amino acid residues 1-269 of SEQ ID NO: 14) from TAT-FAD-hBMP2 such that the Δ(FAD) had only TAT-hBMP2 and a second furin cleavage site; and R283A was obtained by mutating the Arg of the second furin cleavage site of TAT-FAD-hBMP2 to Ala. The N-terminal region of each of the expression vectors contained a TAT domain, a X-press tag, etc., as in the case of Example 1, and after construction, the base sequence of each of the vectors was analyzed.

Figure 14:
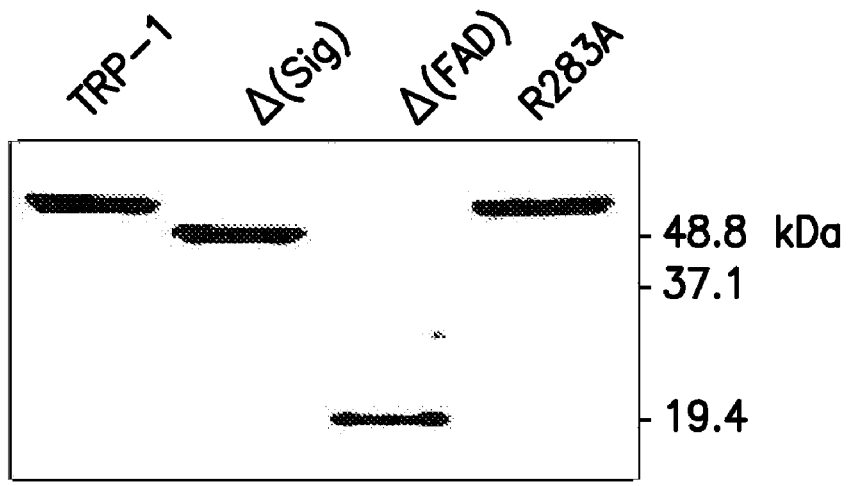
FIG. 14 is a Western blot photograph showing that the inventive TRP-1 and its variant permeate cell membranes to transduce into the cells.

Next, each of the above-prepared TRP-1 and its variants was introduced into the same kind of cells. Namely, primarily cultured fibroblasts were treated with each of the recombinant proteins at a concentration of 2 nM for 2 hours, and the cells were collected and Western-blotted with an anti-X-press antibody (FIG. 14). As a result, as shown in FIG. 14, TRP-1 and its variants were all permeated into the cells and detected.

Example 3

Cleavage and Activation of TRP-1 by Proprotein Convertase

Figure 15:
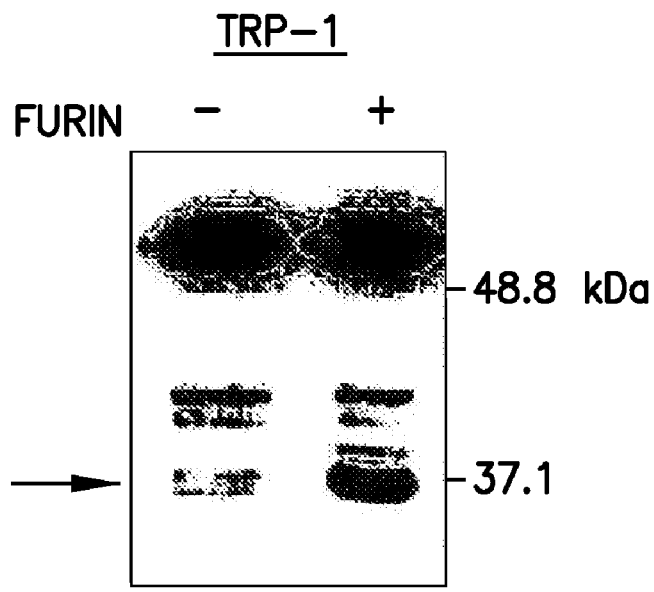
FIG. 15 is a photograph showing that the inventive TRP-1 is cleaved by furin in vitro.

In order to examine whether the inventive non-activated TRP-1 is cleaved and activated by furin in cells, TRP-1 prepared in Example 2 was cleaved in vitro using a recombinant furin protein (Sigma, USA). As a result, as shown in FIG. 15, TRP-1 was successfully cleaved in vitro by the furin.

Also, in order to examine whether the inventive non-activated TRP-1 is activated by furin in cells, intracellular furin was inhibited using α1 antitrypsin Portland (α1-PDX) expression vector (*Proc. Natl. Acad. Sci.*, 95:7293, 1998), as a furin inhibitory protein. Because the inventive non-activated TRP-1 is converted to a biochemically active protein after introduction into cells, the amount of TRP-1 initially introduced into cells shall gradually decrease at a given time after the administration of TRP-1. Thus, it can be expected that, when furin is inhibited by inducing the expression of α1-PDX, the remaining amount of TRP shall increase.

Figure 16:
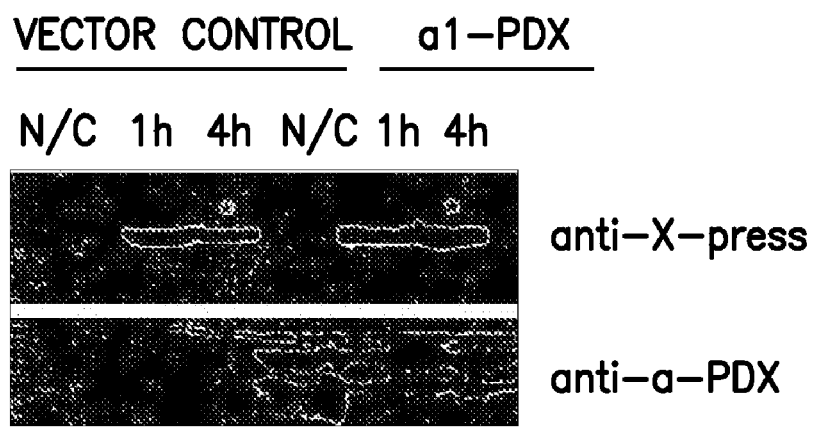
FIG. 16 shows the results of Western blot analysis using α1-PDX and anti-X-press, which indicate that the inventive TRP-1 is activated by furin in cells.

As a result, as shown in FIG. 16, the half-life of the inventive TRP-1 was increased by the expression of α1-PDX (i.e., the inhibition of furin enzyme). Namely, when administered with the inventive TRP-1, the group administered with α1-PDX showed an increase in half life compared to the control group after 4 hours (asterisked). This result suggests that TRP-1 administered into cells is cleaved and activated by furin enzyme.

Example 4

Importance of FAD in Activation of TRP-1

It was confirmed through Examples 2 and 3 that TRP-1 is cleaved and activated by furin in cells. Thus, it can be expected that FAD and the furin cleavage site will play an important role in making the TRP-1 to show biological activity after administration into cells.

Figure 17:
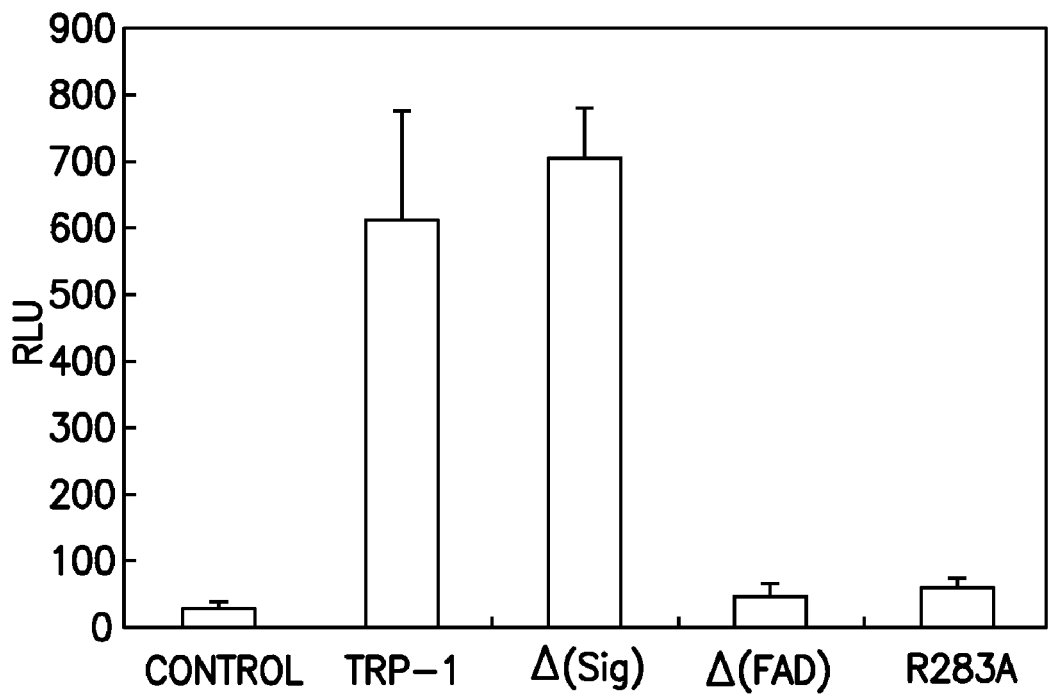
FIG. 17 shows measurement results for ALP activity in fibroblasts treated with the inventive TRP-1 and its variants.

To confirm this expectation, TRP-1 obtained in Example 2 and its variants were added to primarily cultured fibroblasts and observed for ALP activity and the deposition of mineralized substances (FIG. 17). TRP-1 and its variants were measured for alkaline phosphatase (ALP) activity in the same manner as in Example 1, as a result, as shown in FIG. 17, TRP-1 (TAT-FAD-hBMP2) showed high ALP activity, and the TRP-1 variant [Δ(Sig)] from which a signal peptide has been deleted showed a similar or higher activity than that of TRP-1. These results indicate that the signal peptide is not necessary for the activation of BMP2 by TAT and FAD. However, it can be seen that the variant [Δ(FAD)] containing only a second furin activation site in TAT-hBMP2, and the variant (R283A) having a mutation in a portion of the furin cleavage site of TRP-1, had no biological activity.

Figure 18:
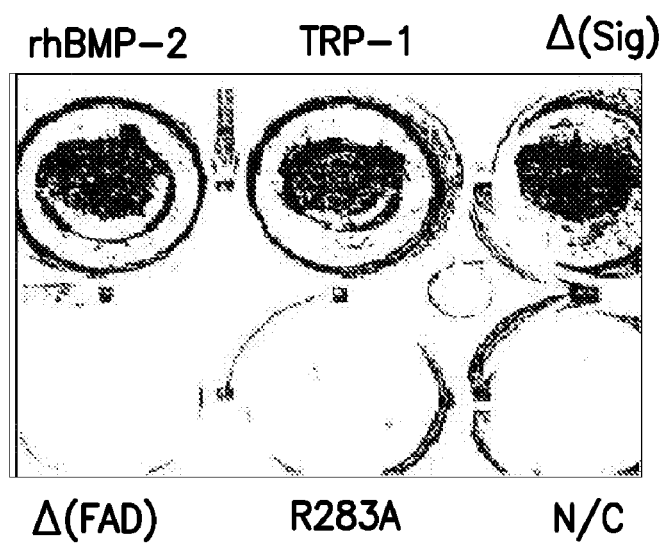
FIG. 18 shows that fibroblasts treated with the inventive TRP-1 and its variants were subjected to von Kossa staining to examine the differentiation of bone cells and the formation of mineralized substances.

Also, each of TRP-1 and its variants were treated for 2 weeks according to the above-described method and stained by the von Kossa method and then observed for the formation of mineralized substances. As a result, as shown in FIG. 18, the mineralization inducing effects were similar to ALP activity. Herein, commercially available rhBMP-2 treated at the same concentration was used as a positive control, and an untreated medium was used as a negative control (N/C). These results suggest that, in order for the TAT-FAD-hBMP2 recombinant protein to permeate into cells and to have biological activity, a process for migration from ribosomes to golgi networks is unnecessary unlike the case of naturally biosynthesized hBMP-2 or rhBMP-2, but the furin cleavage site must be present in a complete and precise manner.

The results of this Example indicate that, when the inventive TAT-FAD-hBMP2 fusion polypeptide has a deletion of any one domain in a polypeptide consisting of 3 domains of PTD, FAD and TRD (hBMP2 in this Example) or has a defect, it cannot exhibit the desired pharmacological effects upon administration into the human body. Although this interpretation of mechanisms for the pharmacological action of TRP-1 (FIG. 6) cannot be complete, it is expected that, when polypeptides, such as non-activated BMPs or TGF-β proteins, are administered into the human body for the purpose for regenerating bones, cartilages or other various tissues, the inventive TRP-1 shall show highly useful pharmacological effects and remarkably high commercial values, compared to previously known products. Namely, the TAT-FAD-hBMP-2 was designed under the concept of new pharmacological actions completely different from previously known BMPs or TGF-β proteins and prepared according to a new method, and was thus named "TRP-1".

Example 5

Preparation of TRP-2[TAT-FAD-BMP7]

As described in Example 4, when secretory proteins, such as BMPs and TGF-β, are fused with PTD, it is insufficient to only make them to have full length, and upon biosynthesis in vivo, they must sufficiently have furin cleavage and activation sites in a precursor formed. Human BMP7 is known to stimulate the differentiation of bones and cartilages, and recently known to act as an antagonist of TGF-β which is a member of the same gene group, thus inhibiting the fibrosis and cirrhosis of kidneys, liver, lungs and heart (*Nature Med.*, 9:964, 2003; *J. Clin. Invest.*, 112:1776, 2003).

In this Example, a base sequence encoding an amino acid sequence comprising FAD of SEQ ID NO: 19 and hBMP7 of SEQ ID NO: 6 was amplified in the same manner as in Example 2 using primers of SEQ ID Nos: 38 and 39. The amplified base sequence was analyzed in GenBank (NCBI, NM_001719), and cloned into a bacterial expression vector in the same manner as in Example 2 so as to prepare a recombinant polypeptide that was then named "TRP-2".

SEQ ID NO: 38: 5'-ggc gcg atg cac gtg cgc tc ctg-3'
SEQ ID NO: 39: 5'-agg gtc tga att ctc gga gga gct-3'

Figure 19:
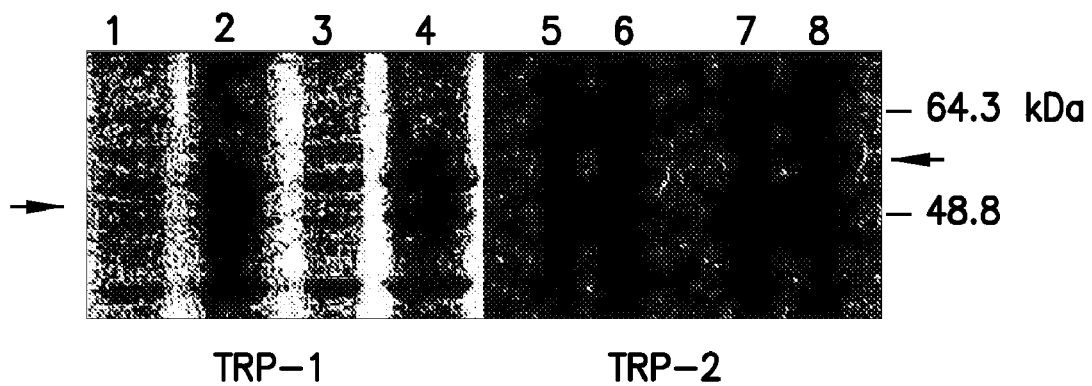
FIG. 19 shows electrophoresis photographs of a total protein before and after inducing TRP-1 and TRP-2 expressions by IPTG during the culture of the inventive recombinant E. coli.

FIG. 19 shows the results of electrophoresis for a total protein before and after inducing the expression of the protein by IPTG in the culture of transformed *E. coli* BL21. In FIG. 19, the arrow represents a TRP fusion protein induced by IPTG; lane 1 represents uninduced TRP-1; lane 2 represents TRP-1 induced by IPTG; lane 3 represents uninduced TRP-1 (w/o TAT); lane 4 represents TRP-1 (w/o TAT) induced by IPTG; lane 5 represents uninduced TRP-2 (w/o TAT); lane 6 represents induced TRP-2 (w/o TAT); lane 7 represents uninduced TRP-2; and lane 8 represents TRP-2 induced by IPTG. As shown in FIG. 19, in the case where the production of fusion proteins by the addition of IPTG was induced, TRPs were induced in larger amounts than that in the control group.

Figure 20:
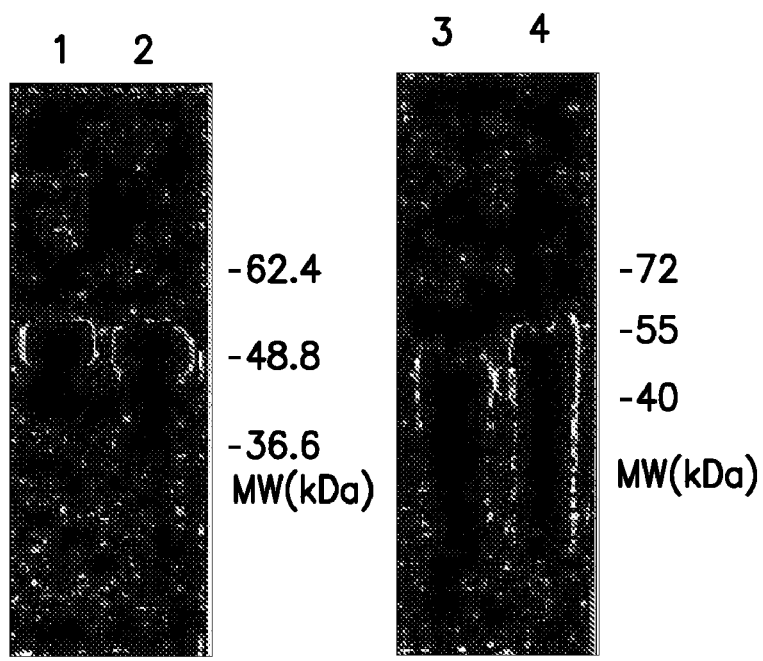
FIG. 20 shows the results of Western blot analysis for the inventive TRP-1 and TRP-2 using an anti-X-press antibody.

FIG. 20 shows the results of Western blot analysis using an anti-X-press antibody for the purified TRPs. In FIG. 20, lanes 1 through 4 represent TRP-1, TRP-1 (w/o TAT), TRP-2 (w/o TAT) and TRP-2, respectively. As shown in FIG. 20, the addition of TAT showed a slight increase in molecular weight compared to the case of no addition, suggesting that the TRP fusion polypeptides were successfully prepared.

Example 6

Intracellular Transduction of TRP-1 and TRP-2

In this Example, primarily cultured gingival fibroblasts were first treated with 4 nM of each of TRP-1 and TRP-2 purified in Examples 2 and 5, and the TRP-1 and TRP-2 present in each of the cells and media were examined for intracellular transduction by comparing their expression levels.

Figure 21:
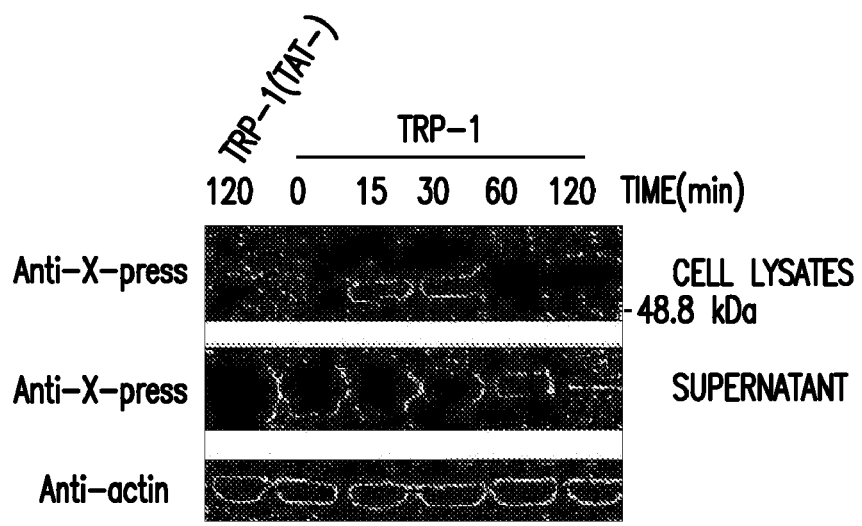
FIG. 21 illustrates the results of Western blot analysis using an anti-X-press antibody, which show the process of the inventive TRP-1 being introduced into cells.
Figure 22:
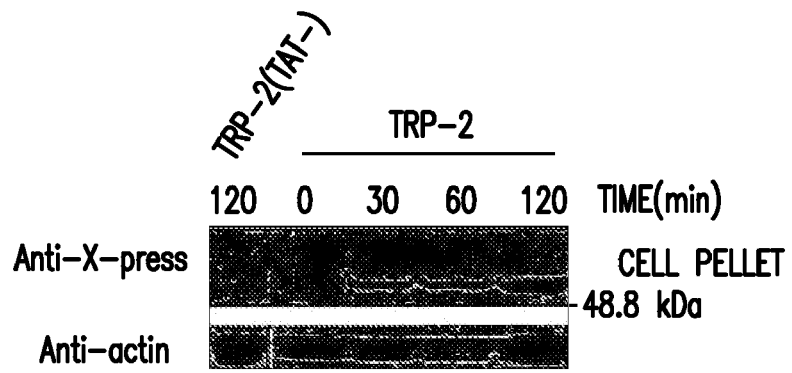
FIG. 22 illustrates the results of Western blot analysis using an anti-X-press antibody, which show the process of the inventive TRP-2 being introduced into cells.

As a result, as shown in FIG. 21, TRP-1 permeated the cell membrane and transduced into cells. Namely, the primarily cultured gingival fibroblasts were first treated with 4 nM of TRP-1, and the expression of TRP-1 present in each of the cell and medium was analyzed by Western blot. As a result, The TRP-1 proteins mostly transduced into the cells within one hour and little remained in the medium after 6 hours. However, the control group having no TAT did not enter the cells at all. Also, TRP-2 was administered into the cells in the same manner. As a result, as shown in FIG. 22, TRP-2 also permeated the cell membrane and transduced into the cells within 2 hours, but the control group having no TAT did not enter the cells at all.

Example 7

Secretion of Activated BMP by TRPs and Importance of PTD

Figure 23:
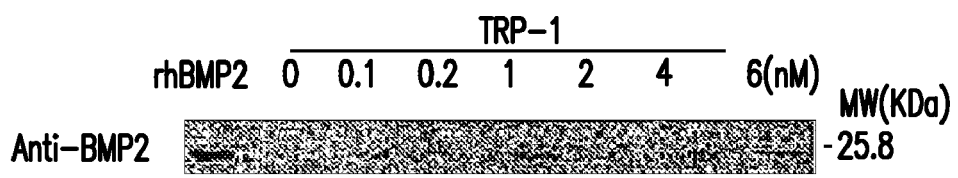
FIG. 23 illustrates the results for Western blot analysis conducted to examine the secretion of activated hBMP2 in fibroblasts treated with the inventive TRP-1.

In this Example, in order to examine whether the activated BMP is secreted in cells introduced with TRPs, TRP-1 was introduced into the cells and measured for the secretion of the activated BMP2 within 48 hours. As a result, as shown in FIG. 23, the TRP-1 introduced into the cells secreted the activated BMP2 within 48 hours. Herein, rhBMP-2, which is a commercially available active BMP2, was used as a positive control.

Figure 24:
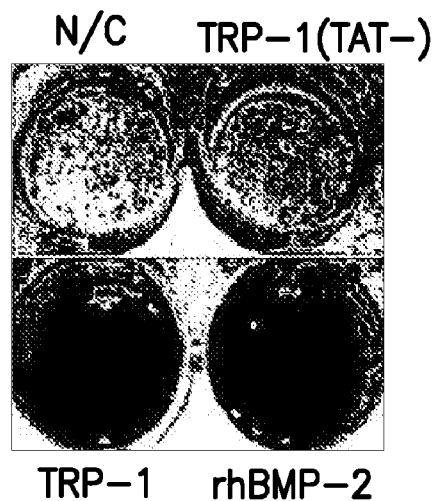
FIG. 24 shows that fibroblasts treated with the inventive TRP-1 and commercially available rhBMP-2 were subjected to von Kossa staining to examine the differentiation of bone cells and the formation of mineralized substances.

Also, the inventive TRP-1 was introduced into the primarily cultured fibroblasts and analyzed for the differentiation of bone cells and the formation of mineralized substances, thus examining effects on the differentiation of bone cells and the regeneration of bones. For this purpose, fibroblasts were cultured for one week, being treated with each of 2 nM of rhBMP-2 and TRP-1 for 2 weeks. After one week, the cells were subjected to von Kossa staining and observed visually, as a result, as shown in FIG. 24, the differentiation of bone cells and the formation of mineralized substances could not be observed in the case of a negative control (N/C) consisting of only the cell culture medium, and TRP-1 having no TAT (i.e., [TRP-1(TAT-)]. However, in the case of TRP-1 and commercially available rhBMP-2, the differentiation of bone cells and the formation of mineralized substances could be observed in the fibroblasts.

Figure 25:
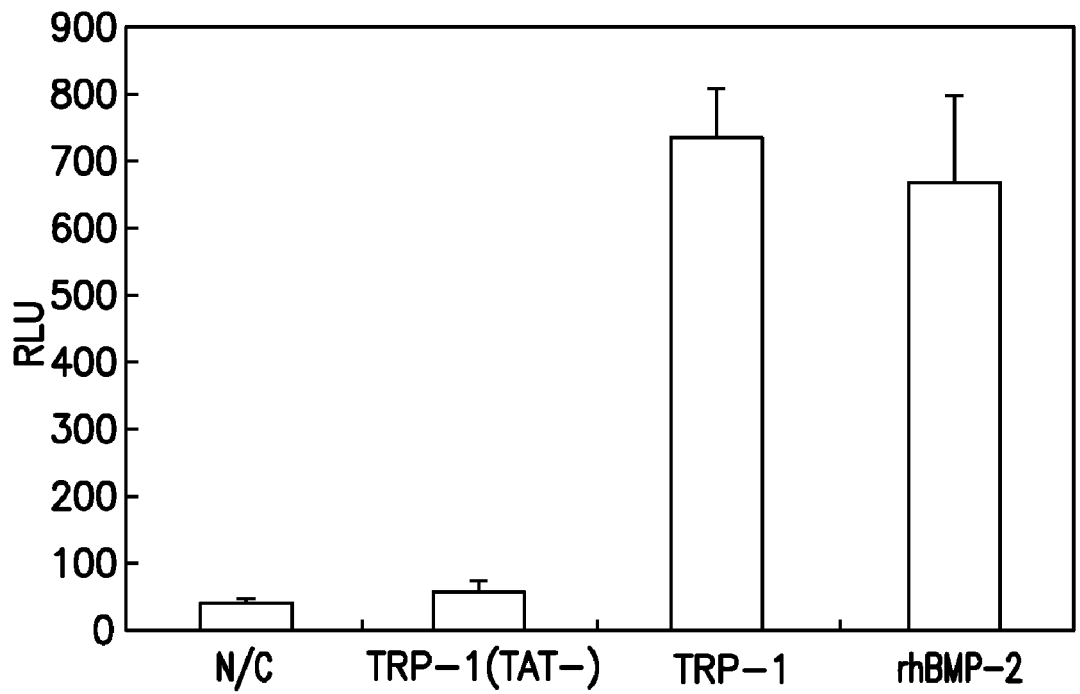
FIG. 25 shows measurement results for ALP activity in fibroblasts treated with the inventive TRP-1 and commercially available rhBMP-2.

In addition, fibroblasts were treated in the same manner for one week and measured for alkaline phosphatase (ALP) activity used as a bone cell differentiation marker. As a result, as shown in FIG. 25, the inventive TRP-1 and the commercially available rhBMP-2 showed similar ALP induction effects.

Figure 26:
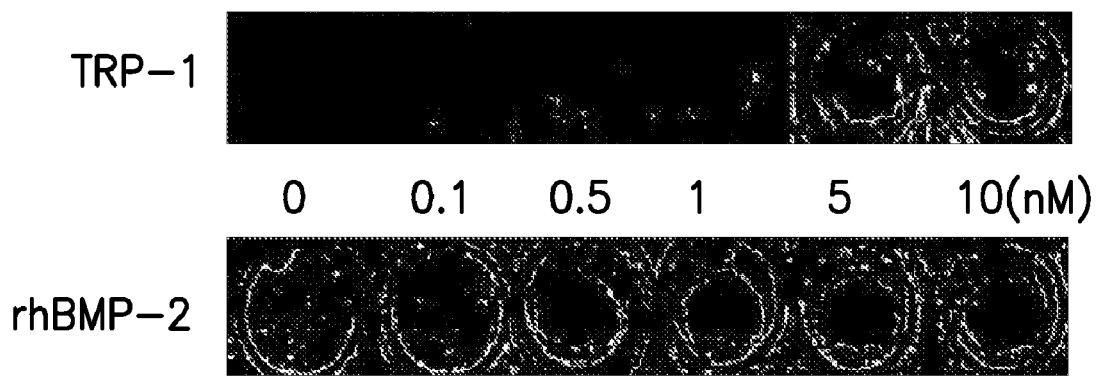
FIG. 26 shows that fibroblasts treated with the TRP-1 and rhBMP-2 at various concentrations were subjected to von Kossa staining to examine the differentiation of bone cells and the formation of mineralized substances.

Meanwhile, in order to compare the potency of the commercially available BMP2 (rhBMP-2) with that of the inventive TRP-1, fibroblasts were cultured for one week, treated with each of TRP-1 and rhBMP-2 and subjected to von Kossa staining, followed by visual observation. As a result, as shown in FIG. 26, the inventive TRP-1 and the activated rhBMP-2 showed similar potencies. Specifically, at concentrations of higher than 0.5 nM, the commercially available rhBMP-2 and the inventive TRP-1 showed similar potencies.

Example 8

Activation Half Life of TRPS after Cell Membrane Permeation

In this Example, in order to confirm that TRPs introduced into cells are secreted in the form of activated BMPs after processes for protein rearrangement by HSPs, etc., and activation by furin, the activation half life of the administered proteins was examined. For this purpose, the 293 cell line (ATCC CRL-1573) having high furin activity was administered with the inventive TRP-1 and treated in the same manner as in Example 6. Then, the expression of the TRP-1 in the cells was analyzed hourly by Western blot.

Figure 27:
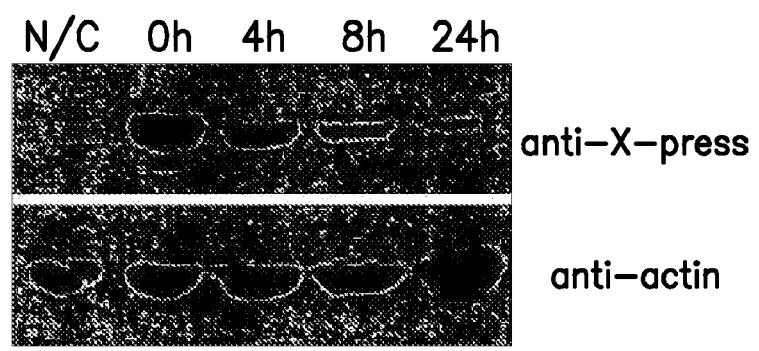
FIG. 27 shows the results of Western blot analysis using an anti-X-press antibody, which indicate the half-life of the inventive TRP-1 introduced into cells.

As a result, as shown in FIG. 27, the TRP-1 administered into the cells had a half-life of 3-4 hours in the 293 cells. The half-life varied depending on the type of cells, in which the half-life was about 6 hours in the osteogenic sarcoma cell line, and about 8 hours in the primarily cultured fibroblasts. These results suggest that the inventive TRPs are secreted in the form of activated BMPs after activation by HSPs, furin, etc., in cells.

Example 9

Cell membrane Permeation of TRPs and Effect of Temperature on Permeation

Figure 28:
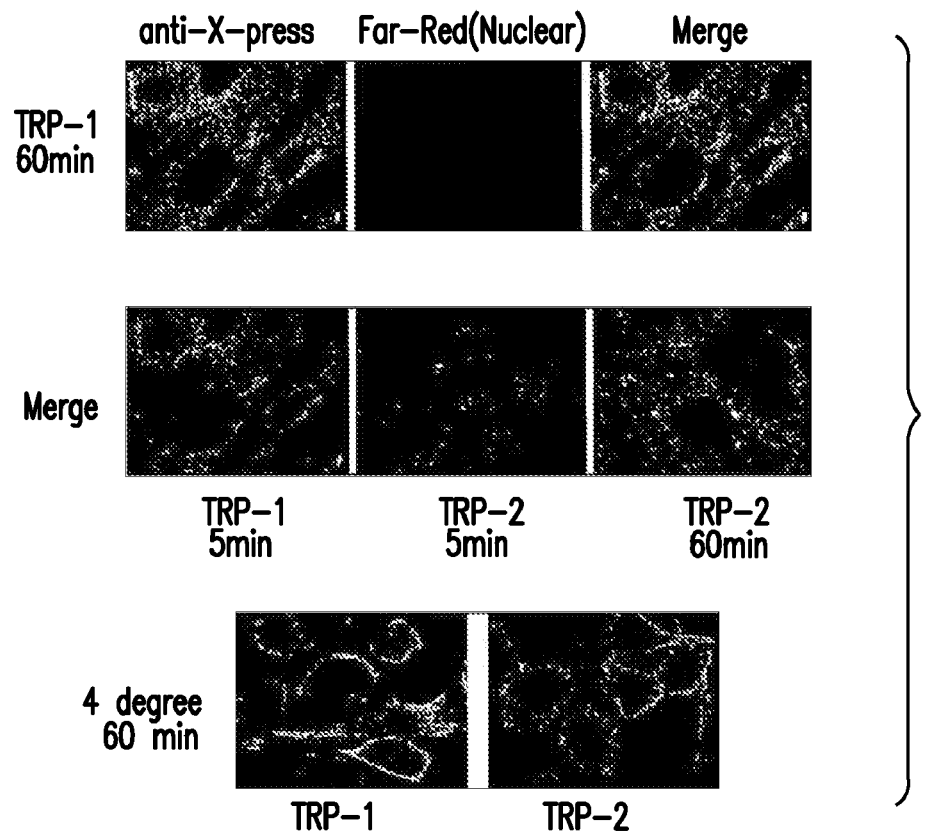
FIG. 28 is a confocal microphotograph showing observation results for the intracellular permeation and temperature effect of the inventive TRP-1 and TRP-2.

The commercially available recombinant rhBMPs pass through receptors present in the cell membrane, but the inventive TRPs directly permeate the cell membrane, and the intracellular permeation of the prior rhBMP-2 through the receptor is dependent on temperature. In order to examine whether the intracellular permeation of the inventive TRPs is dependent on temperature, the inventive TRP-1 and TRP-2 were administered at varying temperatures, and observed with confocal fluorescent microscope at various points in time. Herein, each of the inventive TRP-1 and TRP-2 was used at a constant concentration of 10 nM and treated at various temperatures and time points as shown in FIG. 28. The permeated TRPs were allowed to react with anti-X-press (Invitrogen) as a primary antibody and Alexa-Fluoro-488 (Invitrogen) as a secondary antibody, and their nuclei were stained with Far-Red TOTO-3 (Molecular Probes). The uppermost photographs in FIG. 28 show that TRP-1 entered the cytoplasm at 37° C., and the photograph indicated by "Merge" shows the merged image of the cell nuclei with TRP-1 having the same cross section. Also, the middle photographs show the merged images of TRP-1 treated for 5 min and TRP-2 treated for 5 and 60 min. The lowest photographs show the merged images of TRP-1 and TRP-2 that have been treated at 4° C. for 60 min and transduced into cells.

As a result, as shown in FIG. 28, TRP-1 permeated the cell membrane within 5 minutes after administration at 37° C. After about one hour, TRP-1 and TRP-2 were mostly found in the cytoplasm although they were also partially present in the nuclei. In addition, they also showed permeation patterns at 25° C. and 4° C. in a manner similar to the case of 37° C. These results revealed that that the cell membrane permeation of the inventive TRPs is independent on temperature.

Example 10

Specific Binding Between TRPs Introduced into Cells and F-Actin

Figure 29:
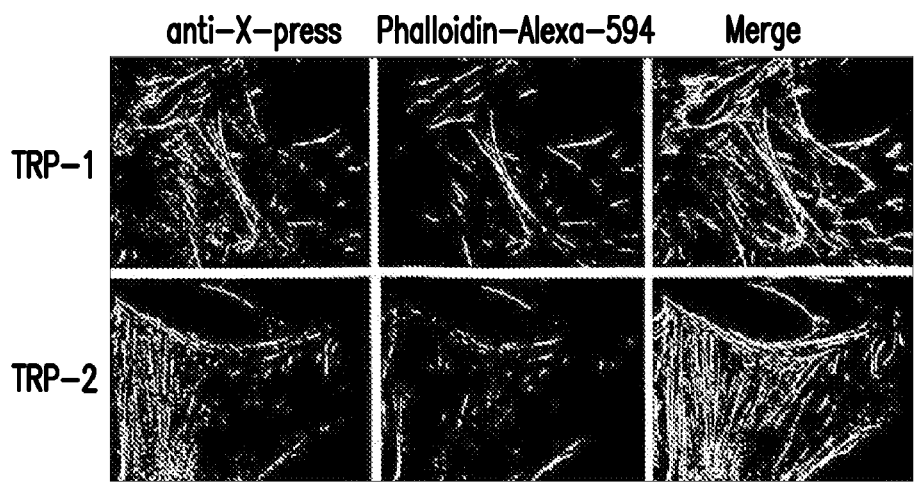
FIG. 29 is a photograph showing that the inventive TRP-1 and TRP-2 specifically bind to F-actin after permeation into cells.

As described above, the inventive TRPs were present in cells in the form of a linear pattern. In this Example, in order to examine whether the inventive TRPs are present specifically in a specific organelle or structure after cell membrane permeation, the TRPs were subjected to immunofluorescent staining using phalloidin specific to a F-actin stress fiber having an arrangement similar to their structure (*Science*, 276:1425, 1997) and observed with a confocal fluorescent microscope (FIG. 29). In this case, TRP-1 and TRP-2 were fluorescence-stained in the same manner as in Example 9, and Phalloidin-Alexa-594 (Molecular Probes) was used for F-actin-specific staining. In FIG. 29, weak blue images in the Merge photographs show the lower portions of cell nuclei.

As a result, as shown in FIG. 29, the inventive TRP-1 and TRP-2, after administration, not only have the same arrangement as that of cellular F-actin, but also are present in the same location as that of F-actin. This indicates that TRPs specifically react and bind with F-actin after permeation into cells. These results revealed that TRPs are not randomly distributed in the cells, but are rather bound specifically to F-actin and are converted to active BMPs through various processes for activation and furin cleavage, when permeated into cells.

Example 11

Induction of Bone Formation by TRPs in Animal Test Models

Figure 30:
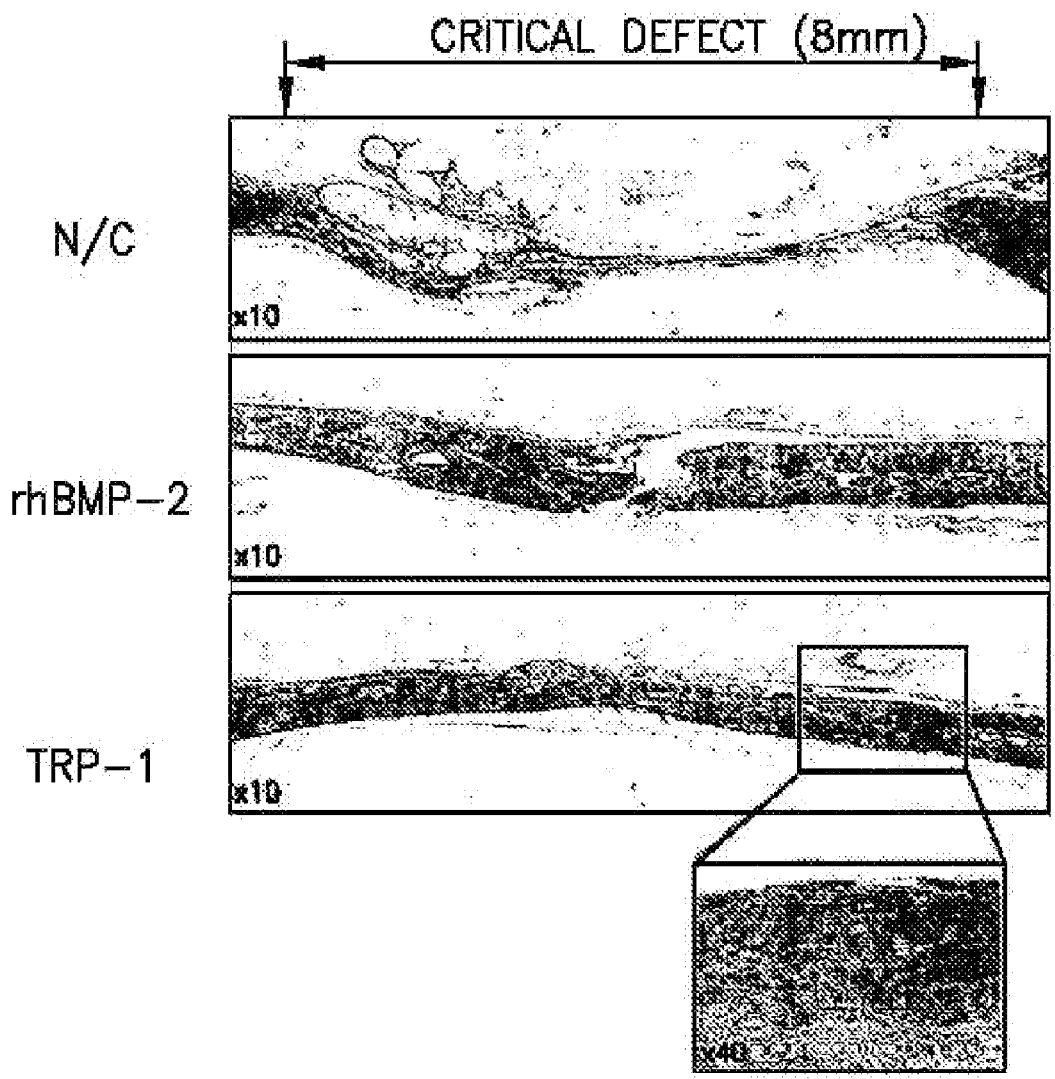
FIG. 30 is a photograph showing that the formation of bones is induced in test animals administered with the inventive TRP-1.

Examples 1 through 10 revealed that the inventive TRP-1 and TRP-2 permeate the cell membrane and are activated by furin, and the activated proteins induce the differentiation of bone cells and the formation of mineralized substances. In this Example, in order to examine whether the inventive TRPs induce bone formation in vivo, a naturally incurable defect (8 mm critical defect) was made in the skull of each of rats. Then, the inventive TRP-1 and the commercially available rhBMP-2 were administered into the defects and observed for the induction of bone formation (FIG. 30). In making the naturally incurable damage in the skull of each rat, 8-mm-diameter trephine was used to the defect. In a negative control, type I collagen was used, and in a positive control (rh-BMP), a mixture of commercially available recombinant BMP2 and type I collagen was used. The inventive TRP-1 was administered in the same manner as the positive control. Also, each of rhBMP-2 and TRP-1 was administered in an amount of 10 nmole. Two weeks after the administration of BMPs, the tissue of each test group was taken and fixed in 10% formalin for 24 hours, and 4-μm sections of the tissue were stained with hematoxylin/eosin and then observed with an optical microscope. In FIG. 30, both the arrows indicate the ends of each bone defect, and the lowest box is an enlarged view of a bone formation site induced by TRP-1.

As a result, as shown in FIG. 30, the differentiation of bone cells and the formation of bones were actively induced in vivo only 2 weeks after administration with the inventive TRP-1.

Also, the administration of TRP-1 showed potency better or at least similar to the commercially available rhBMP-2 administered at the same amount.

Example 12

Cytoxicity of TRPs

Figure 31:
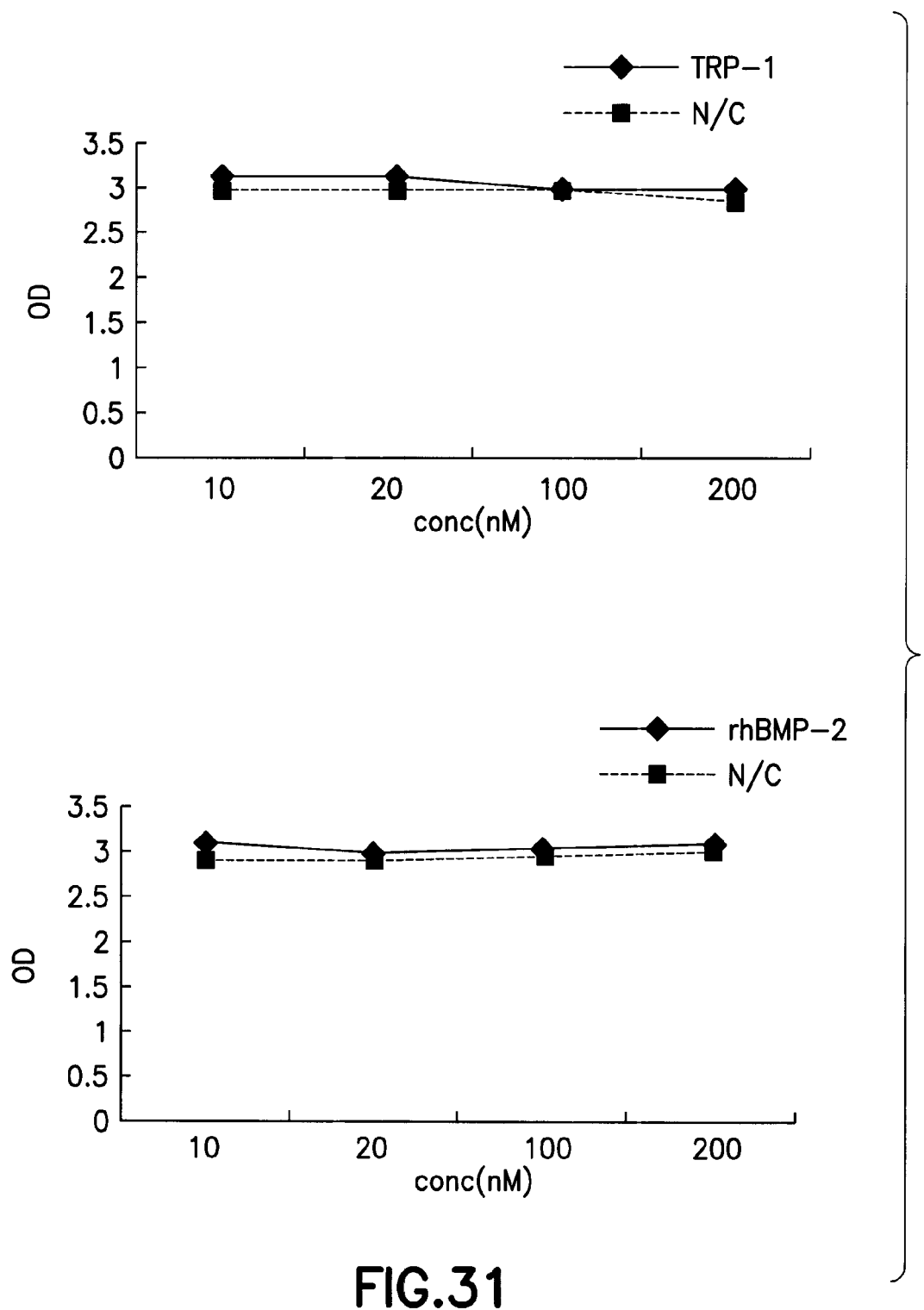
FIG. 31 shows the comparison of cytotoxicity between the inventive TRP-1 and the prior commercially available rhBMP-2.

Examples 1 through 11 presented the mechanisms and potential effects of the inventive TRPs, which result from their administration to cells or tissues. In order to examine cytotoxicity occurring when the inventive TRPs were administered in excess, the inventive TRPs together with the commercially available rhBMP were analyzed for cytotoxicity while increasing their concentration to 200 nM. For this purpose, TRP-1 and recombinant BMP2 were administered to primarily cultured fibroblasts at various concentrations, and 72 hours after the administration, the number of viable cells was counted (FIG. 31). As a result, as shown in FIG. 31, TRP-1 did not showed any cytotoxicity even when it was administered at a concentration of 200 nM.

Although specific embodiment of the present invention was described in detail above, those skilled in the art would appreciate that these descriptions are only intended to give preferred embodiments and are not construed to limit the scope of the present invention. For example, the administration of the inventive TRP-1 to the human body will be useful to stimulate the formation of bones and cartilages, while the administration of the inventive TRP-2 to the human body will be useful not only to stimulate the formation of bones or cartilages, but also to improve the fibrosis and cirrhosis of kidneys, liver, lungs and heart depending on circumstances and administration conditions. Accordingly, the substantial scope of the present invention will be defined by the appended claims and equivalents thereof.

Industrial Applicability

As described in detail above, the present invention provides the non-activated polypeptides having pharmacological mechanisms completely different from those of the prior active proteins. The inventive TRPs have new mechanisms where they are in a non-activated state before in vivo administration but are activated in vivo. Thus, the inventive TRPs do not require additional equipment or cost for maintaining a three-dimensional structure to bind to the cell membrane receptor. In addition, the inventive TRPs are simple to produce, very easy to separate and purify, low in production cost, and also convenient to store, handle and administer. Accordingly, these TRPs can substitute for the prior activated proteins, such as rhBMPs.

What is claimed is:

1. A method for preparing non-activated tissue-regeneration polypeptide (TRP), comprising the steps of:
   (a) culturing transformed bacteria to express [PTD-FAD-TRD] a polypeptide in a culture broth, wherein the transformed bacteria are bacteria transformed with a recombinant bacterial expression vector comprising a furin activation domain (FAD)-encoding base sequence upstream of the 5' region of tissue regeneration domain (TRD)-encoding DNA, a protein transduction domain (PTD) base sequence, a base sequence for tagging, and at least four histidine-encoding base sequences for separation and purification, wherein the PTD is a TAT sequence selected from the group consisting of SEQ ID NOs: 27 and 43, the TRD is an amino acid sequence selected from the group consisting of SEQ ID NOs: 1, 3 and 6 and the FAD is an amino acid sequence selected from the group consisting of SEQ ID NOs: 14 and 19; and
   (b) centrifuging the culture broth;
   (c) removing the secondary or tertiary structure of the polypeptide or converting the secondary or tertiary structure to primary linear structure by the addition of a urea solution into the supernatant and cell pellet to generate a urea, supernatant, cell pellet mixture; and
   (d) separating from the mixture and purifying a non-activated polypeptide.

2. The method for preparing non-activated TRP according to claim 1, wherein the purification step comprises binding the polypeptide to nickel-titanium beads, washing the beads with the urea solution, and then eluting the beads with imidazole and a salt-containing buffer solution.

3. The method for preparing non-activated TRP according to claim 1, wherein the TRD is SEQ ID NO: and the FAD is SEQ ID NO: 14.

4. The method for preparing non-activated TRP according to claim 1, wherein the TRD is SEQ ID NO: 6 and the FAD is SEQ ID NO: 19.

5. A recombinant vector for expression in bacteria, comprising a furin activation domain (FAD)-encoding base sequence upstream of the 5' region of tissue regeneration domain (TRD)-encoding DNA, a protein transduction domain (PTD) base sequence, a base sequence for tagging, and at least four histidine-encoding base sequences for separation and purification,
   wherein the TRD is an amino acid sequence selected from the group consisting of SEQ ID NOs: 1, 3 and 6;
   wherein the FAD is an amino acid sequence selected from the group consisting of SEQ ID NOs: 14 and 19; and
   wherein the PTD is a TAT sequence, selected from the group consisting of SEQ ID NOs: 27 and 43.

* * * * *

SEQUENCE LISTING

```
<160> NUMBER OF SEQ ID NOS: 43

<210> SEQ ID NO 1
<211> LENGTH: 114
<212> TYPE: PRT
<213> ORGANISM: Homo sapiens

<400> SEQUENCE: 1

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30
```

```
Val Ala Pro Pro Gly Tyr His Ala Phe Tyr Cys His Gly Glu Cys Pro
             35                  40                  45

Phe Pro Leu Ala Asp His Leu Asn Ser Thr Asn His Ala Ile Val Gln
 50                  55                  60

Thr Leu Val Asn Ser Val Asn Ser Lys Ile Pro Lys Ala Cys Cys Val
 65                  70                  75                  80

Pro Thr Glu Leu Ser Ala Ile Ser Met Leu Tyr Leu Asp Glu Asn Glu
                 85                  90                  95

Lys Val Val Leu Lys Asn Tyr Gln Asp Met Val Val Glu Gly Cys Thr
                100                 105                 110

Cys Arg

<210> SEQ ID NO 2
<211> LENGTH: 183
<212> TYPE: PRT
<213> ORGANISM: Homo sapiens

<400> SEQUENCE: 2

Ser Thr Gly Val Leu Leu Pro Leu Gln Asn Asn Glu Leu Pro Gly Ala
 1               5                  10                  15

Glu Tyr Gln Tyr Lys Lys Asp Glu Val Trp Glu Arg Lys Pro Tyr
                20                  25                  30

Lys Thr Leu Gln Ala Gln Ala Pro Glu Lys Ser Lys Asn Lys Lys Lys
                 35                  40                  45

Gln Arg Lys Gly Pro His Arg Lys Ser Gln Thr Leu Gln Phe Asp Glu
                 50                  55                  60

Gln Thr Leu Lys Lys Ala Arg Arg Lys Gln Trp Ile Glu Pro Arg Asn
 65                  70                  75                  80

Cys Ala Arg Arg Tyr Leu Lys Val Asp Phe Ala Asp Ile Gly Trp Ser
                 85                  90                  95

Glu Trp Ile Ile Ser Pro Lys Ser Phe Asp Ala Tyr Tyr Cys Ser Gly
                100                 105                 110

Ala Cys Gln Phe Pro Met Pro Lys Ser Leu Lys Pro Ser Asn His Ala
                115                 120                 125

Thr Ile Gln Ser Ile Val Arg Ala Val Gly Val Val Pro Gly Ile Pro
                130                 135                 140

Glu Pro Cys Cys Val Pro Glu Lys Met Ser Ser Leu Ser Ile Leu Phe
145                 150                 155                 160

Phe Asp Glu Asn Lys Asn Val Val Leu Lys Val Tyr Pro Asn Met Thr
                165                 170                 175

Val Glu Ser Cys Ala Cys Arg
                180

<210> SEQ ID NO 3
<211> LENGTH: 116
<212> TYPE: PRT
<213> ORGANISM: Homo sapiens

<400> SEQUENCE: 3

Ser Pro Lys His His Ser Gln Arg Ala Arg Lys Lys Asn Lys Asn Cys
 1               5                  10                  15

Arg Arg His Ser Leu Tyr Val Asp Phe Ser Asp Val Gly Trp Asn Asp
                20                  25                  30

Trp Ile Val Ala Pro Pro Gly Tyr Gln Ala Phe Tyr Cys His Gly Asp
                 35                  40                  45

Cys Pro Phe Pro Leu Ala Asp His Leu Asn Ser Thr Asn His Ala Ile
```

```
                 50                  55                  60
Val Gln Thr Leu Val Asn Ser Val Asn Ser Ser Ile Pro Lys Ala Cys
 65                  70                  75                  80

Cys Val Pro Thr Glu Leu Ser Ala Ile Ser Met Leu Tyr Leu Asp Glu
                     85                  90                  95

Tyr Asp Lys Val Val Leu Lys Asn Tyr Gln Glu Met Val Val Glu Gly
                    100                 105                 110

Cys Gly Cys Arg
            115

<210> SEQ ID NO 4
<211> LENGTH: 138
<212> TYPE: PRT
<213> ORGANISM: Homo sapiens

<400> SEQUENCE: 4

Ala Ala Asn Lys Arg Lys Asn Gln Asn Arg Asn Lys Ser Ser Ser His
 1               5                  10                  15

Gln Asp Ser Ser Arg Met Ser Ser Val Gly Asp Tyr Asn Thr Ser Glu
                20                  25                  30

Gln Lys Gln Ala Cys Lys Lys His Glu Leu Tyr Val Ser Phe Arg Asp
             35                  40                  45

Leu Gly Trp Gln Asp Trp Ile Ile Ala Pro Glu Gly Tyr Ala Ala Phe
 50                  55                  60

Tyr Cys Asp Gly Glu Cys Ser Phe Pro Leu Asn Ala His Met Asn Ala
 65                  70                  75                  80

Thr Asn His Ala Ile Val Gln Thr Leu Val His Leu Met Phe Pro Asp
                 85                  90                  95

His Val Pro Lys Pro Cys Cys Ala Pro Thr Lys Leu Asn Ala Ile Ser
            100                 105                 110

Val Leu Tyr Phe Asp Asp Ser Ser Asn Val Ile Leu Lys Lys Tyr Arg
            115                 120                 125

Asn Met Val Val Arg Ser Cys Gly Cys His
            130                 135

<210> SEQ ID NO 5
<211> LENGTH: 139
<212> TYPE: PRT
<213> ORGANISM: Homo sapiens

<400> SEQUENCE: 5

Ser Ala Ser Ser Arg Arg Arg Gln Gln Ser Arg Asn Arg Ser Thr Gln
 1               5                  10                  15

Ser Gln Asp Val Ala Arg Val Ser Ser Ala Ser Asp Tyr Asn Ser Ser
                20                  25                  30

Glu Leu Lys Thr Ala Cys Arg Lys His Glu Leu Tyr Val Ser Phe Gln
             35                  40                  45

Asp Leu Gly Trp Gln Asp Trp Ile Ile Ala Pro Lys Gly Tyr Ala Ala
     50                  55                  60

Asn Tyr Cys Asp Gly Glu Cys Ser Phe Pro Leu Asn Ala His Met Asn
 65                  70                  75                  80

Ala Thr Asn His Ala Ile Val Gln Thr Leu Val His Leu Met Asn Pro
                 85                  90                  95

Glu Tyr Val Pro Lys Pro Cys Cys Ala Pro Thr Lys Leu Asn Ala Ile
            100                 105                 110

Ser Val Leu Tyr Phe Asp Asp Asn Ser Asn Val Ile Leu Lys Lys Tyr
            115                 120                 125
```

```
Arg Asn Met Val Val Arg Ala Cys Gly Cys His
    130                 135
```

<210> SEQ ID NO 6
<211> LENGTH: 139
<212> TYPE: PRT
<213> ORGANISM: Homo sapiens

<400> SEQUENCE: 6

```
Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Gly His
    130                 135
```

<210> SEQ ID NO 7
<211> LENGTH: 133
<212> TYPE: PRT
<213> ORGANISM: Homo sapiens

<400> SEQUENCE: 7

```
Arg Arg Gln Pro Lys Lys Ser Asn Glu Leu Pro Gln Ala Asn Arg Leu
1               5                   10                  15

Pro Gly Ile Phe Asp Asp Val His Gly Ser His Gly Arg Gln Val Cys
            20                  25                  30

Arg Arg His Glu Leu Tyr Val Ser Phe Gln Asp Leu Gly Trp Leu Asp
        35                  40                  45

Trp Val Ile Ala Pro Gln Gly Tyr Ser Ala Tyr Tyr Cys Glu Gly Glu
    50                  55                  60

Cys Ser Phe Pro Leu Asp Ser Cys Met Asn Ala Thr Asn His Ala Ile
65                  70                  75                  80

Leu Gln Ser Leu Val His Leu Met Met Pro Asp Ala Val Pro Lys Ala
                85                  90                  95

Cys Cys Ala Pro Thr Lys Leu Ser Ala Thr Ser Val Leu Tyr Tyr Asp
            100                 105                 110

Ser Ser Asn Asn Val Ile Leu Arg Lys His Arg Asn Met Val Val Lys
        115                 120                 125

Ala Cys Gly Cys His
    130
```

<210> SEQ ID NO 8
<211> LENGTH: 110
<212> TYPE: PRT
<213> ORGANISM: Homo sapiens -continued

<400> SEQUENCE: 8

Ser Ala Gly Ala Gly Ser His Cys Gln Lys Thr Ser Leu Arg Val Asn
1               5                   10                  15

Phe Glu Asp Ile Gly Trp Asp Ser Trp Ile Ile Ala Pro Lys Glu Tyr
                20                  25                  30

Glu Ala Tyr Glu Cys Lys Gly Gly Cys Phe Phe Pro Leu Ala Asp Asp
            35                  40                  45

Val Thr Pro Thr Lys His Ala Ile Val Gln Thr Leu Val His Leu Lys
    50                  55                  60

Phe Pro Thr Lys Val Gly Lys Ala Cys Cys Val Pro Thr Lys Leu Ser
65                  70                  75                  80

Pro Ile Ser Val Leu Tyr Lys Asp Asp Met Gly Val Pro Thr Leu Lys
                85                  90                  95

Tyr His Tyr Glu Gly Met Ser Val Ala Glu Cys Gly Cys Arg
            100                 105                 110

<210> SEQ ID NO 9
<211> LENGTH: 108
<212> TYPE: PRT
<213> ORGANISM: Homo sapiens

<400> SEQUENCE: 9

Asn Ala Lys Gly Asn Tyr Cys Lys Arg Thr Pro Leu Tyr Ile Asp Phe
1               5                   10                  15

Lys Glu Ile Gly Trp Asp Ser Trp Ile Ile Ala Pro Pro Gly Tyr Glu
                20                  25                  30

Ala Tyr Glu Cys Arg Gly Val Cys Asn Tyr Pro Leu Ala Glu His Leu
            35                  40                  45

Thr Pro Thr Lys His Ala Ile Ile Gln Ala Leu Val His Leu Lys Asn
    50                  55                  60

Ser Gln Lys Ala Ser Lys Ala Cys Cys Val Pro Thr Lys Leu Glu Pro
65                  70                  75                  80

Ile Ser Ile Leu Tyr Leu Asp Lys Gly Val Val Thr Tyr Lys Phe Lys
                85                  90                  95

Tyr Glu Gly Met Ala Val Ser Glu Cys Gly Cys Arg
            100                 105

<210> SEQ ID NO 10
<211> LENGTH: 108
<212> TYPE: PRT
<213> ORGANISM: Homo sapiens

<400> SEQUENCE: 10

Asn Ala Lys Gly Asn Tyr Cys Lys Arg Thr Pro Leu Tyr Ile Asp Phe
1               5                   10                  15

Lys Glu Ile Gly Trp Asp Ser Trp Ile Ile Ala Pro Pro Gly Tyr Glu
                20                  25                  30

Ala Tyr Glu Cys Arg Gly Val Cys Asn Tyr Pro Leu Ala Glu His Leu
            35                  40                  45

Thr Pro Thr Lys His Ala Ile Ile Gln Ala Leu Val His Leu Lys Asn
    50                  55                  60

Ser Gln Lys Ala Ser Lys Ala Cys Cys Val Pro Thr Lys Leu Glu Pro
65                  70                  75                  80

Ile Ser Ile Leu Tyr Leu Asp Lys Gly Val Val Thr Tyr Lys Phe Lys
                85                  90                  95

Tyr Glu Gly Met Ala Val Ser Glu Cys Gly Cys Arg
            100                 105

<210> SEQ ID NO 11
<211> LENGTH: 104
<212> TYPE: PRT
<213> ORGANISM: Homo sapiens

<400> SEQUENCE: 11

```
Ser Arg Cys Ser Arg Lys Pro Leu His Val Asp Phe Lys Glu Leu Gly
1               5                   10                  15

Trp Asp Asp Trp Ile Ile Ala Pro Leu Asp Tyr Glu Ala Tyr His Cys
            20                  25                  30

Glu Gly Leu Cys Asp Phe Pro Leu Arg Ser His Leu Glu Pro Thr Asn
        35                  40                  45

His Ala Ile Ile Gln Thr Leu Leu Asn Ser Met Ala Pro Asp Ala Ala
    50                  55                  60

Pro Ala Ser Cys Cys Val Pro Ala Arg Leu Ser Pro Ile Ser Ile Leu
65                  70                  75                  80

Tyr Ile Asp Ala Ala Asn Asn Val Val Tyr Lys Gln Tyr Glu Asp Met
                85                  90                  95

Val Val Glu Ala Cys Gly Cys Arg
            100
```

<210> SEQ ID NO 12
<211> LENGTH: 120
<212> TYPE: PRT
<213> ORGANISM: Homo sapiens

<400> SEQUENCE: 12

```
Thr Ala Phe Ala Ser Arg His Gly Lys Arg His Gly Lys Lys Ser Arg
1               5                   10                  15

Leu Arg Cys Ser Lys Lys Pro Leu His Val Asn Phe Lys Glu Leu Gly
            20                  25                  30

Trp Asp Asp Trp Ile Ile Ala Pro Leu Glu Tyr Glu Ala Tyr His Cys
        35                  40                  45

Glu Gly Val Cys Asp Phe Pro Leu Arg Ser His Leu Glu Pro Thr Asn
    50                  55                  60

His Ala Ile Ile Gln Thr Leu Met Asn Ser Met Asp Pro Gly Ser Thr
65                  70                  75                  80

Pro Pro Ser Cys Cys Val Pro Thr Lys Leu Thr Pro Ile Ser Ile Leu
                85                  90                  95

Tyr Ile Asp Ala Gly Asn Asn Val Val Thr Lys Gln Tyr Glu Asp Met
            100                 105                 110

Val Val Glu Ser Cys Gly Cys Arg
        115                 120
```

<210> SEQ ID NO 13
<211> LENGTH: 120
<212> TYPE: PRT
<213> ORGANISM: Homo sapiens

<400> SEQUENCE: 13

```
Ala Pro Leu Ala Thr Arg Gln Gly Lys Arg Pro Ser Lys Asn Leu Lys
1               5                   10                  15

Ala Arg Cys Ser Arg Lys Ala Leu His Val Asn Phe Lys Asp Met Gly
            20                  25                  30

Trp Asp Asp Trp Ile Ile Ala Pro Leu Glu Tyr Glu Ala Phe His Cys
        35                  40                  45

Glu Gly Leu Cys Glu Phe Pro Leu Arg Ser His Leu Glu Pro Thr Asn
```

```
                 50                  55                  60
His Ala Val Ile Gln Thr Leu Met Asn Ser Met Asp Pro Glu Ser Thr
 65                  70                  75                  80

Pro Pro Thr Cys Cys Val Pro Thr Arg Leu Ser Pro Ile Ser Ile Leu
                 85                  90                  95

Phe Ile Asp Ser Ala Asn Asn Val Val Tyr Lys Gln Tyr Glu Asp Met
            100                 105                 110

Val Val Glu Ser Cys Gly Cys Arg
        115                 120

<210> SEQ ID NO 14
<211> LENGTH: 281
<212> TYPE: PRT
<213> ORGANISM: Homo sapiens

<400> SEQUENCE: 14

Met Val Ala Gly Thr Arg Cys Leu Leu Ala Leu Leu Leu Pro Gln Val
  1               5                  10                  15

Leu Leu Gly Gly Ala Ala Gly Leu Val Pro Glu Leu Gly Arg Arg Lys
             20                  25                  30

Phe Ala Ala Ala Ser Ser Gly Arg Pro Ser Ser Gln Pro Ser Asp Glu
         35                  40                  45

Val Leu Ser Glu Phe Glu Leu Arg Leu Leu Ser Met Phe Gly Leu Lys
 50                  55                  60

Gln Arg Pro Thr Pro Ser Arg Asp Ala Val Val Pro Pro Tyr Met Leu
 65                  70                  75                  80

Asp Leu Tyr Arg Arg His Ser Gly Gln Pro Gly Ser Pro Ala Pro Asp
                 85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gly His Ala Asn His Gly
    210                 215                 220

Phe Val Val Glu Val Ala His Leu Glu Glu Lys Gln Gly Val Ser Lys
225                 230                 235                 240

Arg His Val Arg Ile Ser Arg Ser Leu His Gln Asp Glu His Ser Trp
                245                 250                 255

Ser Gln Ile Arg Pro Leu Leu Val Thr Phe Gly His Asp Gly Lys Gly
            260                 265                 270

His Pro Leu His Lys Arg Glu Lys Arg
        275                 280

<210> SEQ ID NO 15
<211> LENGTH: 289
<212> TYPE: PRT
```

<213> ORGANISM: Homo sapiens

<400> SEQUENCE: 15

Met Ala Gly Ala Ser Arg Leu Leu Phe Leu Trp Gly Cys Phe Cys
1               5                   10                  15

Val Ser Leu Ala Gln Gly Glu Arg Pro Lys Pro Pro Phe Pro Glu Leu
                20                  25                  30

Arg Lys Ala Val Pro Gly Asp Arg Thr Ala Gly Gly Pro Asp Ser
            35                  40                  45

Glu Leu Gln Pro Gln Asp Lys Val Ser Glu His Met Leu Arg Leu Tyr
    50                  55                  60

Asp Arg Tyr Ser Thr Val Gln Ala Ala Arg Thr Pro Gly Ser Leu Glu
65              70                  75                  80

Gly Gly Ser Gln Pro Trp Arg Pro Arg Leu Leu Arg Glu Gly Asn Thr
                85                  90                  95

Val Arg Ser Phe Arg Ala Ala Ala Glu Thr Leu Glu Arg Lys Gly
                100                 105                 110

Leu Tyr Ile Phe Asn Leu Thr Ser Leu Thr Lys Ser Glu Asn Ile Leu
            115                 120                 125

Ser Ala Thr Leu Tyr Phe Cys Ile Gly Glu Leu Gly Asn Ile Ser Leu
    130                 135                 140

Ser Cys Pro Val Ser Gly Gly Cys Ser His His Ala Gln Arg Lys His
145                 150                 155                 160

Ile Gln Ile Asp Leu Ser Ala Trp Thr Leu Lys Phe Ser Arg Asn Gln
                165                 170                 175

Ser Gln Leu Leu Gly His Leu Ser Val Asp Met Ala Lys Ser His Arg
            180                 185                 190

Asp Ile Met Ser Trp Leu Ser Lys Asp Ile Thr Gln Phe Leu Arg Lys
        195                 200                 205

Ala Lys Glu Asn Glu Glu Phe Leu Ile Gly Phe Asn Ile Thr Ser Lys
    210                 215                 220

Gly Arg Gln Leu Pro Lys Arg Leu Pro Phe Pro Glu Pro Tyr Ile
225                 230                 235                 240

Leu Val Tyr Ala Asn Asp Ala Ala Ile Ser Glu Pro Glu Ser Val Val
                245                 250                 255

Ser Ser Leu Gln Gly His Arg Asn Phe Pro Thr Gly Thr Val Pro Lys
            260                 265                 270

Trp Asp Ser His Ile Arg Ala Ala Leu Ser Ile Glu Arg Arg Lys Lys
        275                 280                 285

Arg

<210> SEQ ID NO 16
<211> LENGTH: 292
<212> TYPE: PRT
<213> ORGANISM: Homo sapiens

<400> SEQUENCE: 16

Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
                20                  25                  30

Lys Lys Val Ala Gly Ile Gln Gly His Ala Gly Gly Arg Arg Ser Gly
            35                  40                  45

Gln Ser His Glu Leu Leu Arg Asp Phe Glu Ala Thr Leu Leu Gln Met
    50                  55                  60

```
Phe Gly Leu Arg Arg Arg Pro Gln Pro Ser Lys Ser Ala Val Ile Pro
 65                  70                  75                  80

Asp Tyr Met Arg Asp Leu Tyr Arg Leu Gln Ser Gly Glu Glu Glu
                85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
            115                 120                 125

Ile Pro Gly Thr Ser Glu Asn Ser Ala Phe Arg Phe Leu Phe Asn Leu
            130                 135                 140

Ser Ser Ile Pro Glu Asn Glu Ala Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
                180                 185                 190

Gly His Leu Ile Thr Arg Leu Leu Asp Thr Arg Leu Val His His Asn
            195                 200                 205

Val Thr Arg Trp Glu Thr Phe Asp Val Ser Pro Ala Val Leu Arg Trp
210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
                260                 265                 270

Val Thr Phe Gly His Asp Gly Arg Gly His Ala Leu Thr Arg Arg Arg
                275                 280                 285

Arg Ala Lys Arg
            290

<210> SEQ ID NO 17
<211> LENGTH: 316
<212> TYPE: PRT
<213> ORGANISM: Homo sapiens

<400> SEQUENCE: 17

Met His Leu Thr Val Phe Leu Leu Lys Gly Ile Val Gly Phe Leu Trp
  1               5                  10                  15

Ser Cys Trp Val Leu Val Gly Tyr Ala Lys Gly Gly Leu Gly Asp Asn
                 20                 25                  30

His Val His Ser Ser Phe Ile Tyr Arg Arg Leu Arg Asn His Glu Arg
             35                  40                  45

Arg Glu Ile Gln Arg Glu Ile Leu Ser Ile Leu Gly Leu Pro His Arg
 50                  55                  60

Pro Arg Pro Phe Ser Pro Gly Lys Gln Ala Ser Ser Ala Pro Leu Phe
 65                  70                  75                  80

Met Leu Asp Leu Tyr Asn Ala Met Thr Asn Glu Glu Asn Pro Glu Glu
                 85                  90                  95

Ser Glu Tyr Ser Val Arg Ala Ser Leu Ala Glu Glu Thr Arg Gly Ala
            100                 105                 110

Arg Lys Gly Tyr Pro Ala Ser Pro Asn Gly Tyr Pro Arg Arg Ile Gln
            115                 120                 125

Leu Ser Arg Thr Thr Pro Leu Thr Thr Gln Ser Pro Pro Leu Ala Ser
            130                 135                 140
```

```
Leu His Asp Thr Asn Phe Leu Asn Asp Ala Asp Met Val Met Ser Phe
145                 150                 155                 160

Val Asn Leu Val Glu Arg Asp Leu Asp Phe Ser His Gln Arg Arg His
            165                 170                 175

Tyr Lys Glu Phe Arg Phe Asp Leu Thr Gln Ile Pro His Gly Glu Ala
        180                 185                 190

Val Thr Ala Ala Glu Phe Arg Ile Tyr Lys Asp Arg Ser Asn Asn Arg
    195                 200                 205

Phe Glu Asn Glu Thr Ile Lys Ile Ser Ile Tyr Gln Ile Ile Lys Glu
210                 215                 220

Tyr Thr Asn Arg Asp Ala Asp Leu Phe Leu Leu Asp Thr Arg Lys Ala
225                 230                 235                 240

Gln Ala Leu Asp Val Gly Trp Leu Val Phe Asp Ile Thr Val Thr Ser
            245                 250                 255

Asn His Trp Val Ile Asn Pro Gln Asn Asn Leu Gly Leu Gln Leu Cys
        260                 265                 270

Ala Glu Thr Gly Asp Gly Arg Ser Ile Asn Val Lys Ser Ala Gly Leu
    275                 280                 285

Val Gly Arg Gln Gly Pro Gln Ser Lys Gln Pro Phe Met Val Ala Phe
290                 295                 300

Phe Lys Ala Ser Glu Val Leu Leu Arg Ser Val Arg
305                 310                 315

<210> SEQ ID NO 18
<211> LENGTH: 374
<212> TYPE: PRT
<213> ORGANISM: Homo sapiens

<400> SEQUENCE: 18

Met Pro Gly Leu Gly Arg Arg Ala Gln Trp Leu Cys Trp Trp Trp Gly
1               5                   10                  15

Leu Leu Cys Ser Cys Cys Gly Pro Pro Leu Arg Pro Pro Leu Pro
            20                  25                  30

Ala Ala Ala Ala Ala Ala Gly Gly Gln Leu Leu Gly Asp Gly Gly
            35                  40                  45

Ser Pro Gly Arg Thr Glu Gln Pro Pro Ser Pro Gln Ser Ser Ser
    50                  55                  60

Gly Phe Leu Tyr Arg Arg Leu Lys Thr Gln Glu Lys Arg Gly Met Gln
65                  70                  75                  80

Lys Glu Ile Leu Ser Val Leu Gly Leu Pro His Arg Pro Arg Pro Leu
            85                  90                  95

His Gly Leu Gln Gln Pro Gln Pro Pro Ala Leu Arg Gln Gln Glu Glu
        100                 105                 110

Gln Gln Gln Gln Gln Gln Leu Pro Arg Gly Glu Pro Pro Pro Gly Arg
    115                 120                 125

Leu Lys Ser Ala Pro Leu Phe Met Leu Asp Leu Tyr Asn Ala Leu Ser
    130                 135                 140

Ala Asp Asn Asp Glu Asp Gly Ala Ser Glu Gly Glu Arg Gln Gln Ser
145                 150                 155                 160

Trp Pro His Glu Ala Ala Ser Ser Ser Gln Arg Arg Gln Pro Pro Pro
            165                 170                 175

Gly Ala Ala His Pro Leu Asn Arg Lys Ser Leu Leu Ala Pro Gly Ser
        180                 185                 190

Gly Ser Gly Gly Ala Ser Pro Leu Thr Ser Ala Gln Asp Ser Ala Phe
    195                 200                 205
```

-continued

```
Leu Asn Asp Ala Asp Met Val Met Ser Phe Val Asn Leu Val Glu Tyr
    210                 215                 220

Asp Lys Glu Phe Ser Pro Arg Gln Arg His His Lys Glu Phe Lys Phe
225                 230                 235                 240

Asn Leu Ser Gln Ile Pro Glu Gly Ile Val Thr Ala Ala Glu Phe
                245                 250                 255

Arg Ile Tyr Lys Asp Cys Val Met Gly Ser Phe Lys Asn Gln Thr Phe
                260                 265                 270

Leu Ile Ser Ile Tyr Gln Val Leu Gln Glu His Gln His Arg Asp Ser
                275                 280                 285

Asp Leu Phe Leu Leu Asp Thr Arg Val Val Trp Ala Ser Glu Glu Gly
    290                 295                 300

Trp Leu Glu Phe Asp Ile Thr Ala Thr Ser Asn Leu Trp Val Val Thr
305                 310                 315                 320

Pro Gln His Asn Met Gly Leu Gln Leu Ser Val Val Thr Arg Asp Gly
                325                 330                 335

Val His Val His Pro Arg Ala Ala Gly Leu Val Gly Arg Asp Gly Pro
                340                 345                 350

Tyr Asp Lys Gln Pro Phe Met Val Ala Phe Lys Val Ser Glu Val
                355                 360                 365

His Val Arg Thr Thr Arg
    370

<210> SEQ ID NO 19
<211> LENGTH: 292
<212> TYPE: PRT
<213> ORGANISM: Homo sapiens

<400> SEQUENCE: 19

Met His Val Arg Ser Leu Arg Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
                35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
                100                 105                 110

Thr Gln Gly Pro Pro Leu Ala Ser Leu Gln Asp Ser His Phe Leu Thr
    115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
                180                 185                 190

Ser Val Tyr Gln Val Leu Gln Glu His Leu Gly Arg Glu Ser Asp Leu
                195                 200                 205
```

```
Phe Leu Leu Asp Ser Arg Thr Leu Trp Ala Ser Glu Glu Gly Trp Leu
            210                 215                 220
Val Phe Asp Ile Thr Ala Thr Ser Asn His Trp Val Val Asn Pro Arg
225                 230                 235                 240
His Asn Leu Gly Leu Gln Leu Ser Val Glu Thr Leu Asp Gly Gln Ser
                245                 250                 255
Ile Asn Pro Lys Leu Ala Gly Leu Ile Gly Arg His Gly Pro Gln Asn
            260                 265                 270
Lys Gln Pro Phe Met Val Ala Phe Lys Ala Thr Glu Val His Phe
            275                 280                 285
Arg Ser Ile Arg
    290

<210> SEQ ID NO 20
<211> LENGTH: 269
<212> TYPE: PRT
<213> ORGANISM: Homo sapiens

<400> SEQUENCE: 20

Met Thr Ala Leu Pro Gly Pro Leu Trp Leu Leu Gly Leu Ala Leu Cys
1               5                   10                  15
Ala Leu Gly Gly Gly Pro Gly Leu Arg Pro Pro Gly Cys Pro
                20                  25                  30
Gln Arg Arg Leu Gly Ala Arg Glu Arg Arg Asp Val Gln Arg Glu Ile
            35                  40                  45
Leu Ala Val Leu Gly Leu Pro Gly Arg Pro Arg Pro Arg Ala Pro Pro
        50                  55                  60
Ala Ala Ser Arg Leu Pro Ala Ser Ala Pro Leu Phe Met Leu Asp Leu
65                  70                  75                  80
Tyr His Ala Met Ala Gly Asp Asp Asp Glu Asp Gly Ala Pro Ala Glu
                85                  90                  95
Arg Arg Leu Gly Arg Ala Asp Leu Val Met Ser Phe Val Asn Met Val
            100                 105                 110
Glu Arg Asp Arg Ala Leu Gly His Gln Glu Pro His Trp Lys Glu Phe
        115                 120                 125
Arg Phe Asp Leu Thr Gln Ile Pro Ala Gly Glu Ala Val Thr Ala Ala
130                 135                 140
Glu Phe Arg Ile Tyr Lys Val Pro Ser Ile His Leu Leu Asn Arg Thr
145                 150                 155                 160
Leu His Val Ser Met Phe Gln Val Val Gln Glu Gln Ser Asn Arg Glu
                165                 170                 175
Ser Asp Leu Phe Phe Leu Asp Leu Gln Thr Leu Arg Ala Gly Asp Glu
            180                 185                 190
Gly Trp Leu Val Leu Asp Val Thr Ala Ala Ser Asp Cys Trp Leu Leu
        195                 200                 205
Lys Arg His Lys Asp Leu Gly Leu Arg Leu Tyr Val Glu Thr Glu Asp
210                 215                 220
Gly His Ser Val Asp Pro Gly Leu Ala Gly Leu Leu Gly Gln Arg Ala
225                 230                 235                 240
Pro Arg Ser Gln Gln Pro Phe Val Val Thr Phe Phe Arg Ala Ser Pro
                245                 250                 255
Ser Pro Ile Arg Thr Pro Arg Ala Val Arg Pro Leu Arg
            260                 265

<210> SEQ ID NO 21
<211> LENGTH: 318
```

<212> TYPE: PRT
<213> ORGANISM: Homo sapiens

<400> SEQUENCE: 21

Met Cys Pro Gly Ala Leu Trp Val Ala Leu Pro Leu Leu Ser Leu Leu
1               5                   10                  15

Ala Gly Ser Leu Gln Gly Lys Pro Leu Gln Ser Trp Gly Arg Gly Ser
            20                  25                  30

Ala Gly Gly Asn Ala His Ser Pro Leu Gly Val Pro Gly Gly Gly Leu
        35                  40                  45

Pro Glu His Thr Phe Asn Leu Lys Met Phe Leu Glu Asn Val Lys Val
    50                  55                  60

Asp Phe Leu Arg Ser Leu Asn Leu Ser Gly Val Pro Ser Gln Asp Lys
65                  70                  75                  80

Thr Arg Val Glu Pro Pro Gln Tyr Met Ile Asp Leu Tyr Asn Arg Tyr
                85                  90                  95

Thr Ser Asp Lys Ser Thr Pro Ala Ser Asn Ile Val Arg Ser Phe Ser
                100                 105                 110

Met Glu Asp Ala Ile Ser Ile Thr Ala Thr Glu Asp Phe Pro Phe Gln
            115                 120                 125

Lys His Ile Leu Leu Phe Asn Ile Ser Ile Pro Arg His Glu Gln Ile
        130                 135                 140

Thr Arg Ala Glu Leu Arg Leu Tyr Val Ser Cys Gln Asn His Val Asp
145                 150                 155                 160

Pro Ser His Asp Leu Lys Gly Ser Val Val Ile Tyr Asp Val Leu Asp
                165                 170                 175

Gly Thr Asp Ala Trp Asp Ser Ala Thr Glu Thr Lys Thr Phe Leu Val
            180                 185                 190

Ser Gln Asp Ile Gln Asp Glu Gly Trp Glu Thr Leu Glu Val Ser Ser
        195                 200                 205

Ala Val Lys Arg Trp Val Arg Ser Asp Ser Thr Lys Ser Lys Asn Lys
    210                 215                 220

Leu Glu Val Thr Val Glu Ser His Arg Lys Gly Cys Asp Thr Leu Asp
225                 230                 235                 240

Ile Ser Val Pro Pro Gly Ser Arg Asn Leu Pro Phe Phe Val Val Phe
                245                 250                 255

Ser Asn Asp His Ser Ser Gly Thr Lys Glu Thr Arg Leu Glu Leu Arg
            260                 265                 270

Glu Met Ile Ser His Glu Gln Glu Ser Val Leu Lys Lys Leu Ser Lys
        275                 280                 285

Asp Gly Ser Thr Glu Ala Gly Glu Ser Ser His Glu Glu Asp Thr Asp
    290                 295                 300

Gly His Val Ala Ala Gly Ser Thr Leu Ala Arg Arg Lys Arg
305                 310                 315

<210> SEQ ID NO 22
<211> LENGTH: 316
<212> TYPE: PRT
<213> ORGANISM: Homo sapiens

<400> SEQUENCE: 22

Met Gly Ser Leu Val Leu Thr Leu Cys Ala Leu Phe Cys Leu Ala Ala
1               5                   10                  15

Tyr Leu Val Ser Gly Ser Pro Ile Met Asn Leu Glu Gln Ser Pro Leu
            20                  25                  30

Glu Glu Asp Met Ser Leu Phe Gly Asp Val Phe Ser Glu Gln Asp Gly

```
                35                  40                  45
Val Asp Phe Asn Thr Leu Leu Gln Ser Met Lys Asp Glu Phe Leu Lys
 50                  55                  60

Thr Leu Asn Leu Ser Asp Ile Pro Thr Gln Asp Ser Ala Lys Val Asp
 65                  70                  75                  80

Pro Pro Glu Tyr Met Leu Glu Leu Tyr Asn Lys Phe Ala Thr Asp Arg
                 85                  90                  95

Thr Ser Met Pro Ser Ala Asn Ile Ile Arg Ser Phe Lys Asn Glu Asp
                100                 105                 110

Leu Phe Ser Gln Pro Val Ser Phe Asn Gly Leu Arg Lys Tyr Pro Leu
            115                 120                 125

Leu Phe Asn Val Ser Ile Pro His His Glu Glu Val Ile Met Ala Glu
            130                 135                 140

Leu Arg Leu Tyr Thr Leu Val Gln Arg Asp Arg Met Ile Tyr Asp Gly
145                 150                 155                 160

Val Asp Arg Lys Ile Thr Ile Phe Glu Val Leu Glu Ser Lys Gly Asp
                165                 170                 175

Asn Glu Gly Glu Arg Asn Met Leu Val Leu Val Ser Gly Glu Ile Tyr
            180                 185                 190

Gly Thr Asn Ser Glu Trp Glu Thr Phe Asp Val Thr Asp Ala Ile Arg
            195                 200                 205

Arg Trp Gln Lys Ser Gly Ser Ser Thr His Gln Leu Glu Val His Ile
210                 215                 220

Glu Ser Lys His Asp Glu Ala Glu Asp Ala Ser Ser Gly Arg Leu Glu
225                 230                 235                 240

Ile Asp Thr Ser Ala Gln Asn Lys His Asn Pro Leu Leu Ile Val Phe
                245                 250                 255

Ser Asp Asp Gln Ser Ser Asp Lys Glu Arg Lys Glu Glu Leu Asn Glu
            260                 265                 270

Met Ile Ser His Glu Gln Leu Pro Glu Leu Asp Asn Leu Gly Leu Asp
            275                 280                 285

Ser Phe Ser Ser Gly Pro Gly Glu Glu Ala Leu Leu Gln Met Arg Ser
            290                 295                 300

Asn Ile Ile Tyr Asp Ser Thr Ala Arg Ile Arg Arg
305                 310                 315

<210> SEQ ID NO 23
<211> LENGTH: 316
<212> TYPE: PRT
<213> ORGANISM: Homo sapiens

<400> SEQUENCE: 23

Met Gly Ser Leu Val Leu Thr Leu Cys Ala Leu Phe Cys Leu Ala Ala
 1               5                  10                  15

Tyr Leu Val Ser Gly Ser Pro Ile Met Asn Leu Glu Gln Ser Pro Leu
                20                  25                  30

Glu Glu Asp Met Ser Leu Phe Gly Asp Val Phe Ser Glu Gln Asp Gly
            35                  40                  45

Val Asp Phe Asn Thr Leu Leu Gln Ser Met Lys Asp Glu Phe Leu Lys
 50                  55                  60

Thr Leu Asn Leu Ser Asp Ile Pro Thr Gln Asp Ser Ala Lys Val Asp
 65                  70                  75                  80

Pro Pro Glu Tyr Met Leu Glu Leu Tyr Asn Lys Phe Ala Thr Asp Arg
                 85                  90                  95

Thr Ser Met Pro Ser Ala Asn Ile Ile Arg Ser Phe Lys Asn Glu Asp
```

```
                        100                 105                 110
Leu Phe Ser Gln Pro Val Ser Phe Asn Gly Leu Arg Lys Tyr Pro Leu
            115                 120                 125

Leu Phe Asn Val Ser Ile Pro His His Glu Val Ile Met Ala Glu
        130                 135                 140

Leu Arg Leu Tyr Thr Leu Val Gln Arg Asp Arg Met Ile Tyr Asp Gly
145                 150                 155                 160

Val Asp Arg Lys Ile Thr Ile Phe Glu Val Leu Glu Ser Lys Gly Asp
                165                 170                 175

Asn Glu Gly Glu Arg Asn Met Leu Val Leu Val Ser Gly Glu Ile Tyr
            180                 185                 190

Gly Thr Asn Ser Glu Trp Glu Thr Phe Asp Val Thr Asp Ala Ile Arg
            195                 200                 205

Arg Trp Gln Lys Ser Gly Ser Ser Thr His Gln Leu Glu Val His Ile
        210                 215                 220

Glu Ser Lys His Asp Glu Ala Glu Asp Ala Ser Ser Gly Arg Leu Glu
225                 230                 235                 240

Ile Asp Thr Ser Ala Gln Asn Lys His Asn Pro Leu Leu Ile Val Phe
                245                 250                 255

Ser Asp Asp Gln Ser Ser Asp Lys Glu Arg Lys Glu Glu Leu Asn Glu
            260                 265                 270

Met Ile Ser His Glu Gln Leu Pro Glu Glu Asp Asn Leu Gly Leu Asp
            275                 280                 285

Ser Phe Ser Ser Gly Pro Gly Glu Glu Ala Leu Leu Gln Met Arg Ser
        290                 295                 300

Asn Ile Ile Tyr Asp Ser Thr Ala Arg Ile Arg Arg
305                 310                 315

<210> SEQ ID NO 24
<211> LENGTH: 346
<212> TYPE: PRT
<213> ORGANISM: Homo sapiens

<400> SEQUENCE: 24

Met Asp Leu Ser Ala Ala Ala Leu Cys Leu Trp Leu Leu Ser Ala
1               5                   10                  15

Cys Arg Pro Arg Asp Gly Leu Glu Ala Ala Val Leu Arg Ala Ala
            20                  25                  30

Gly Ala Gly Pro Val Arg Ser Pro Gly Gly Gly Gly Gly Gly Gly
        35                  40                  45

Gly Gly Arg Thr Leu Ala Gln Ala Gly Ala Ala Val Pro Ala
50                  55                  60

Ala Ala Val Pro Arg Ala Arg Ala Arg Arg Ala Gly Ser Gly
65                  70                  75                  80

Phe Arg Asn Gly Ser Val Val Pro His His Phe Met Met Ser Leu Tyr
            85                  90                  95

Arg Ser Leu Ala Gly Arg Ala Pro Ala Gly Ala Ala Val Ser Ala
        100                 105                 110

Ser Gly His Gly Arg Ala Asp Thr Ile Thr Gly Phe Thr Asp Gln Ala
        115                 120                 125

Thr Gln Asp Glu Ser Ala Ala Glu Thr Gly Gln Ser Phe Leu Phe Asp
        130                 135                 140

Val Ser Ser Leu Asn Asp Ala Asp Glu Val Val Gly Ala Glu Leu Arg
145                 150                 155                 160

Val Leu Arg Arg Gly Ser Pro Glu Ser Gly Pro Gly Ser Trp Thr Ser
```

```
                    165                 170                 175
Pro Pro Leu Leu Leu Leu Ser Thr Cys Pro Gly Ala Ala Arg Ala Pro
            180                 185                 190

Arg Leu Leu Tyr Ser Arg Ala Ala Glu Pro Leu Val Gly Gln Arg Trp
        195                 200                 205

Glu Ala Phe Asp Val Ala Asp Ala Met Arg Arg His Arg Arg Glu Pro
    210                 215                 220

Arg Pro Pro Arg Ala Phe Cys Leu Leu Arg Ala Val Ala Gly Pro
225                 230                 235                 240

Val Pro Ser Pro Leu Ala Leu Arg Arg Leu Gly Phe Gly Trp Pro Gly
            245                 250                 255

Gly Gly Gly Ser Ala Ala Glu Glu Arg Ala Val Leu Val Ser Ser
        260                 265                 270

Arg Thr Gln Arg Lys Glu Ser Leu Phe Arg Glu Ile Arg Ala Gln Ala
        275                 280                 285

Arg Ala Leu Gly Ala Ala Leu Ala Ser Glu Pro Leu Pro Asp Pro Gly
        290                 295                 300

Thr Gly Thr Ala Ser Pro Arg Ala Val Ile Gly Gly Arg Arg Arg Arg
305                 310                 315                 320

Arg Thr Ala Leu Ala Gly Thr Arg Thr Ala Gln Gly Ser Gly Gly
                325                 330                 335

Ala Gly Arg Gly His Gly Arg Arg Gly Arg
            340                 345

<210> SEQ ID NO 25
<211> LENGTH: 335
<212> TYPE: PRT
<213> ORGANISM: Homo sapiens

<400> SEQUENCE: 25

Met Asp Thr Pro Arg Val Leu Leu Ser Ala Val Phe Leu Ile Ser Phe
1               5                   10                  15

Leu Trp Asp Leu Pro Gly Phe Gln Gln Ala Ser Ile Ser Ser Ser Ser
            20                  25                  30

Ser Ser Ala Glu Leu Gly Ser Thr Lys Gly Met Arg Ser Arg Lys Glu
        35                  40                  45

Gly Lys Met Gln Arg Ala Pro Arg Asp Ser Asp Ala Gly Arg Glu Gly
    50                  55                  60

Gln Glu Pro Gln Pro Arg Pro Gln Asp Glu Pro Arg Ala Gln Gln Pro
65                  70                  75                  80

Arg Ala Gln Glu Pro Pro Gly Arg Gly Pro Arg Val Val Pro His Glu
            85                  90                  95

Tyr Met Leu Ser Ile Tyr Arg Thr Tyr Ser Ile Ala Glu Lys Leu Gly
            100                 105                 110

Ile Asn Ala Ser Phe Phe Gln Ser Ser Lys Ser Ala Asn Thr Ile Thr
        115                 120                 125

Ser Phe Val Asp Arg Gly Leu Asp Asp Leu Ser His Thr Pro Leu Arg
    130                 135                 140

Arg Gln Lys Tyr Leu Phe Asp Val Ser Met Leu Ser Asp Lys Glu Glu
145                 150                 155                 160

Leu Val Gly Ala Glu Leu Arg Leu Phe Arg Gln Ala Pro Ser Ala Pro
            165                 170                 175

Trp Gly Pro Pro Ala Gly Pro Leu His Val Gln Leu Phe Pro Cys Leu
        180                 185                 190

Ser Pro Leu Leu Leu Asp Ala Arg Thr Leu Asp Pro Gln Gly Ala Pro
```

```
                    195                 200                 205
Pro Ala Gly Trp Glu Asx Phe Asp Val Trp Gln Gly Leu Arg His Gln
            210                 215                 220

Pro Trp Lys Gln Leu Cys Leu Glu Leu Arg Ala Ala Trp Gly Glu Leu
225                 230                 235                 240

Asp Ala Gly Glu Ala Glu Ala Arg Ala Arg Gly Pro Gln Pro Pro
            245                 250                 255

Pro Pro Asp Leu Arg Ser Leu Gly Phe Gly Arg Val Arg Pro Pro
            260                 265                 270

Gln Glu Arg Ala Leu Leu Val Val Phe Thr Arg Ser Gln Arg Lys Asn
            275                 280                 285

Leu Phe Ala Glu Met Arg Glu Gln Leu Gly Ser Ala Glu Ala Gly
            290                 295                 300

Pro Gly Ala Gly Ala Gly Ser Trp Pro Pro Ser Gly Ala Pro
305                 310                 315                 320

Asp Ala Arg Pro Trp Leu Pro Ser Pro Gly Arg Arg Arg Arg
            325                 330                 335

<210> SEQ ID NO 26
<211> LENGTH: 381
<212> TYPE: PRT
<213> ORGANISM: Homo sapiens

<400> SEQUENCE: 26

Met Arg Leu Pro Lys Leu Leu Thr Phe Leu Leu Trp Tyr Leu Ala Trp
1               5                   10                  15

Leu Asp Leu Glu Phe Ile Cys Thr Val Leu Gly Ala Pro Asp Leu Gly
            20                  25                  30

Gln Arg Pro Gln Gly Thr Arg Pro Gly Leu Ala Lys Ala Glu Ala Lys
        35                  40                  45

Glu Arg Pro Pro Leu Ala Arg Asn Val Phe Arg Pro Gly Gly His Ser
    50                  55                  60

Tyr Gly Gly Gly Ala Thr Asn Ala Asn Ala Arg Ala Lys Gly Gly Thr
65                  70                  75                  80

Gly Gln Thr Gly Gly Leu Thr Gln Pro Lys Lys Asp Glu Pro Lys Lys
                85                  90                  95

Leu Pro Pro Arg Pro Gly Gly Pro Glu Pro Lys Pro Gly His Pro Pro
            100                 105                 110

Gln Thr Arg Gln Ala Thr Ala Arg Thr Val Thr Pro Lys Gly Gln Leu
        115                 120                 125

Pro Gly Gly Lys Ala Pro Pro Lys Ala Gly Ser Val Pro Ser Ser Phe
    130                 135                 140

Leu Leu Lys Lys Ala Arg Glu Pro Gly Pro Pro Arg Glu Pro Lys Glu
145                 150                 155                 160

Pro Phe Arg Pro Pro Pro Ile Thr Pro His Glu Tyr Met Leu Ser Leu
                165                 170                 175

Tyr Arg Thr Leu Ser Asp Ala Asp Arg Lys Gly Gly Asn Ser Ser Val
            180                 185                 190

Lys Leu Glu Ala Gly Leu Ala Asn Thr Ile Thr Ser Phe Ile Asp Lys
        195                 200                 205

Gly Gln Asp Asp Arg Gly Pro Val Val Arg Lys Gln Arg Tyr Val Phe
    210                 215                 220

Asp Ile Ser Ala Leu Glu Lys Asp Gly Leu Leu Gly Ala Glu Leu Arg
225                 230                 235                 240

Ile Leu Arg Lys Lys Pro Ser Asp Thr Ala Lys Pro Ala Ala Pro Gly
```

-continued

```
                     245                 250                 255
Gly Gly Arg Ala Ala Gln Leu Lys Leu Ser Ser Cys Pro Ser Gly Arg
            260                 265                 270

Gln Pro Ala Ser Leu Leu Asp Val Arg Ser Val Pro Gly Leu Asp Gly
        275                 280                 285

Ser Gly Trp Glu Val Phe Asp Ile Trp Lys Leu Phe Arg Asn Phe Lys
    290                 295                 300

Asn Ser Ala Gln Leu Cys Leu Glu Leu Glu Ala Trp Glu Arg Gly Arg
305                 310                 315                 320

Ala Val Asp Leu Arg Gly Leu Gly Phe Asp Arg Ala Ala Arg Gln Val
                325                 330                 335

Lys Glu Lys Ala Leu Phe Leu Val Phe Gly Arg Thr Lys Lys Arg Asp
            340                 345                 350

Leu Phe Phe Asn Glu Ile Lys Ala Arg Ser Gly Gln Asp Asp Lys Thr
        355                 360                 365

Val Tyr Glu Tyr Leu Phe Ser Gln Arg Arg Lys Arg Arg
    370                 375                 380

<210> SEQ ID NO 27
<211> LENGTH: 11
<212> TYPE: PRT
<213> ORGANISM: Artificial Sequence
<220> FEATURE:
<223> OTHER INFORMATION: TAT base sequence

<400> SEQUENCE: 27

Tyr Gly Arg Lys Lys Arg Arg Gln Arg Arg Arg
1               5                   10

<210> SEQ ID NO 28
<211> LENGTH: 24
<212> TYPE: DNA
<213> ORGANISM: Artificial Sequence
<220> FEATURE:
<223> OTHER INFORMATION: primer

<400> SEQUENCE: 28
caagccaaac acaaacagcg gaaa                                          24

<210> SEQ ID NO 29
<211> LENGTH: 24
<212> TYPE: DNA
<213> ORGANISM: Artificial Sequence
<220> FEATURE:
<223> OTHER INFORMATION: primer

<400> SEQUENCE: 29
tttgctgtac tagcgacacc caca                                          24

<210> SEQ ID NO 30
<211> LENGTH: 24
<212> TYPE: DNA
<213> ORGANISM: Artificial Sequence
<220> FEATURE:
<223> OTHER INFORMATION: primer

<400> SEQUENCE: 30 gagttttttcc atgtggacgc tctt                                         24

<210> SEQ ID NO 31
<211> LENGTH: 24
<212> TYPE: DNA
<213> ORGANISM: Artificial Sequence
```

```
<220> FEATURE:
<223> OTHER INFORMATION: primer

<400> SEQUENCE: 31
tttgctgtac tagcgacacc caca                                              24

<210> SEQ ID NO 32
<211> LENGTH: 36
<212> TYPE: DNA
<213> ORGANISM: Artificial Sequence
<220> FEATURE:
<223> OTHER INFORMATION: primer

<400> SEQUENCE: 32
tccaccatgg ccggtaccct cgttccggag ctgggc                                 36

<210> SEQ ID NO 33
<211> LENGTH: 36
<212> TYPE: DNA
<213> ORGANISM: Artificial Sequence
<220> FEATURE:
<223> OTHER INFORMATION: primer

<400> SEQUENCE: 33
gcccagctcc ggaacgaggg taccggccat ggtgga                                 36

<210> SEQ ID NO 34
<211> LENGTH: 36
<212> TYPE: DNA
<213> ORGANISM: Artificial Sequence
<220> FEATURE:
<223> OTHER INFORMATION: primer

<400> SEQUENCE: 34
tccaccatgg ccggtaccga tggaaaaggg catcct                                 36

<210> SEQ ID NO 35
<211> LENGTH: 36
<212> TYPE: DNA
<213> ORGANISM: Artificial Sequence
<220> FEATURE:
<223> OTHER INFORMATION: primer

<400> SEQUENCE: 35
aggatgccct tttccatcgg taccggccat ggtgga                                 36

<210> SEQ ID NO 36
<211> LENGTH: 39
<212> TYPE: DNA
<213> ORGANISM: Artificial Sequence
<220> FEATURE:
<223> OTHER INFORMATION: primer

<400> SEQUENCE: 36
ctccacaaaa gagaaaaagc tcaagccaaa cacaaacag                              39

<210> SEQ ID NO 37
<211> LENGTH: 39
<212> TYPE: DNA
<213> ORGANISM: Artificial Sequence
<220> FEATURE:
<223> OTHER INFORMATION: primer

<400> SEQUENCE: 37
ctgtttgtgt ttggcttgag ctttttctct tttgtggag                              39
```

```
<210> SEQ ID NO 38
<211> LENGTH: 23
<212> TYPE: DNA
<213> ORGANISM: Artificial Sequence
<220> FEATURE:
<223> OTHER INFORMATION: primer

<400> SEQUENCE: 38
ggcgcgatgc acgtgcgctc ctg                                    23

<210> SEQ ID NO 39
<211> LENGTH: 24
<212> TYPE: DNA
<213> ORGANISM: Artificial Sequence
<220> FEATURE:
<223> OTHER INFORMATION: primer

<400> SEQUENCE: 39
agggtctgaa ttctcggagg agct                                   24

<210> SEQ ID NO 40
<211> LENGTH: 116
<212> TYPE: PRT
<213> ORGANISM: Homo sapiens

<400> SEQUENCE: 40

Ala Asn Val Ala Glu Asn Ser Ser Asp Gln Arg Gln Ala Cys Lys
1               5                   10                  15

Lys His Glu Leu Tyr Val Ser Phe Arg Asp Leu Gly Trp Gln Asp Trp
            20                  25                  30

Ile Ile Ala Pro Glu Gly Tyr Ala Ala Tyr Tyr Cys Glu Gly Glu Cys
        35                  40                  45

Ala Phe Pro Leu Asn Ser Tyr Met Asn Ala Thr Asn His Ala Ile Val
    50                  55                  60

Gln Thr Leu Val His Phe Ile Asn Pro Glu Thr Val Pro Lys Pro Cys
65                  70                  75                  80

Cys Ala Pro Thr Gln Leu Asn Ala Ile Ser Val Leu Tyr Phe Asp Asp
                85                  90                  95

Ser Ser Asn Val Ile Leu Lys Lys Tyr Arg Asn Met Val Val Arg Ala
            100                 105                 110

Cys Gly Cys His
        115

<210> SEQ ID NO 41
<211> LENGTH: 112
<212> TYPE: PRT
<213> ORGANISM: Homo sapiens

<400> SEQUENCE: 41

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95
```

```
Lys Ile Glu Gln Leu Ser Asn Met Ile Val Lys Ser Cys Lys Cys Ser
            100                 105                 110

<210> SEQ ID NO 42
<211> LENGTH: 112
<212> TYPE: PRT
<213> ORGANISM: Homo sapiens

<400> SEQUENCE: 42

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
            35                  40                  45

Pro Tyr Leu Arg Ser Ala Asp Thr Thr His Ser Thr Val Leu Gly Leu
50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
            85                  90                  95

Lys Val Glu Gln Leu Ser Asn Met Val Val Lys Ser Cys Lys Cys Ser
            100                 105                 110

<210> SEQ ID NO 43
<211> LENGTH: 11
<212> TYPE: PRT
<213> ORGANISM: Artificial Sequence
<220> FEATURE:
<223> OTHER INFORMATION: TAT base sequence

<400> SEQUENCE: 43

Tyr Gly Arg Asp Asp Arg Arg Gln Arg Arg Arg
1               5                   10
```